United States Patent [19]
Sliwa, Jr. et al.

[11] Patent Number: 6,122,538
[45] Date of Patent: Sep. 19, 2000

[54] MOTION—MONITORING METHOD AND SYSTEM FOR MEDICAL DEVICES

[75] Inventors: John William Sliwa, Jr., Los Altos; Paul E. Chandler, Santa Cruz; John D. Marshall, Redwood City; Gelston Howell, Saratoga; S. Lawrence Marple, Jr., San Diego; Sassan Shahidi, San Jose, all of Calif.

[73] Assignee: Acuson Corporation, Mountain View, Calif.

[21] Appl. No.: 08/784,973

[22] Filed: Jan. 16, 1997

[51] Int. Cl.[7] .............................. A61B 19/00; G01C 23/00
[52] U.S. Cl. .................... 600/407; 600/459; 324/207.14; 702/150; 73/510
[58] Field of Search .................................... 128/899, 903, 128/916; 600/407, 424, 459, 117, 595; 606/130; 901/47, 14, 32; 324/207.13, 7.14, 247; 702/94, 95, 150–154; 73/504.03, 510, 511

[56] References Cited

U.S. PATENT DOCUMENTS

| | | |
|---|---|---|
| 3,086,390 | 4/1963 | Brown . |
| 3,777,740 | 12/1973 | Hokanson . |
| 4,058,001 | 11/1977 | Waxman . |
| 4,431,007 | 2/1984 | Amazeen et al. . |
| 4,534,221 | 8/1985 | Fife et al. . |
| 5,050,608 | 9/1991 | Watanabe et al. . |
| 5,078,145 | 1/1992 | Furuhata . |
| 5,159,931 | 11/1992 | Pini . |

(List continued on next page.)

FOREIGN PATENT DOCUMENTS

| | | |
|---|---|---|
| 2 159 278 | 11/1985 | United Kingdom . |
| 2 314 163 | 12/1997 | United Kingdom . |

OTHER PUBLICATIONS

Leotta, D. et al, "Three Dimensional Ultrasound Imaging Using Multiple Magnetic Tracking Systems and Miniature Magnetic Sensors," IEEE Ultrasonics Symposium, pp. 1415–1418, 1995.

Detmer, P. et al., "3D Ultrasonic Image Feature Localization Based on Magnetic Scanhead Tracking: *In Vitro* Calibration and Validation," Ultrasound in Med. & Biol., No. 9, pp. 923–936, 1994.

Shinozuka, N. et al., "Transvaginal Sonographic Orientation Detection System Using Ceramic Gyroscopes," Ultrasound Med. 15, pp. 107–113, 1996.

Applied Physics Systems Model 544 product brochure for Miniature Angular Orientation Sensor, one page, date unknown.

Hansen, K., "A Next–Generation Miniature Pointing Device," Sensor Solutions, pp. 32–37, 1994.

Arley, D., "A Sourceless Orientation Sensor," Sensor Solutions, p. 55, 1993.

*Primary Examiner*—Marvin M. Lateef
*Assistant Examiner*—Shawna J Shaw
*Attorney, Agent, or Firm*—Brinks, Hofer, Gilson & Lione

[57] ABSTRACT

A system and method for tracking the position and orientation of a movable medical imaging device using a first and second sensor disposed on the device. The second sensor is of a different type than the first sensor and measures a P/O parameter different from that of the first sensor. The system and method also include techniques for recalibrating sensors using measurements from other sensors and improving the measurements made by some sensors using measurements from other sensors. The system and method also include measuring the position of a medical implement relative to a movable medical imaging device by providing a first and second subsystem on the medical implement and a third and fourth subsystem on the movable medical imaging device. The first subsystem has a sensor of a first type and the second subsystem has a sensor of a second type different from the sensor of the first type. The third subsystem has a sensor of a third type and the fourth subsystem has a sensor of a fourth type different from the third type.

66 Claims, 16 Drawing Sheets

U.S. PATENT DOCUMENTS

| | | |
|---|---|---|
| 5,240,011 | 8/1993 | Assa . |
| 5,295,486 | 3/1994 | Wollschläger et al. . |
| 5,299,288 | 3/1994 | Glassman et al. . |
| 5,315,512 | 5/1994 | Roth . |
| 5,329,929 | 7/1994 | Sato et al. . |
| 5,339,799 | 8/1994 | Kami et al. . |
| 5,353,354 | 10/1994 | Keller et al. . |
| 5,412,619 | 5/1995 | Bauer . |
| 5,425,367 | 6/1995 | Shapiro et al. . |
| 5,465,724 | 11/1995 | Sliwa, Jr. et al. . |
| 5,505,204 | 4/1996 | Picot et al. . |
| 5,526,022 | 6/1996 | Donahue et al. . |
| 5,529,070 | 6/1996 | Augustine et al. . |
| 5,538,004 | 7/1996 | Bamber . |
| 5,540,229 | 7/1996 | Collet-Billon et al. . |
| 5,558,091 | 9/1996 | Acker et al. . |
| 5,572,513 | 11/1996 | Acker et al. . |
| 5,592,401 | 1/1997 | Kramer ................................. 364/550 |
| 5,592,939 | 1/1997 | Martinelli . |
| 5,609,485 | 3/1997 | Bergman et al. ....................... 434/262 |
| 5,615,132 | 3/1997 | Horton et al. ......................... 364/516 |
| 5,617,857 | 4/1997 | Chader et al. . |
| 5,626,595 | 5/1997 | Sklar et al. ........................... 606/170 |
| 5,638,819 | 6/1997 | Manwaring et al. . |
| 5,645,077 | 7/1997 | Foxlin . |
| 5,728,044 | 3/1998 | Shan . |
| 5,735,282 | 4/1998 | Hossack . |
| 5,739,431 | 4/1998 | Petri . |
| 5,762,064 | 6/1998 | Polvani . |
| 5,810,735 | 9/1998 | Halperin et al. . |
| 5,831,260 | 11/1998 | Hensen . |

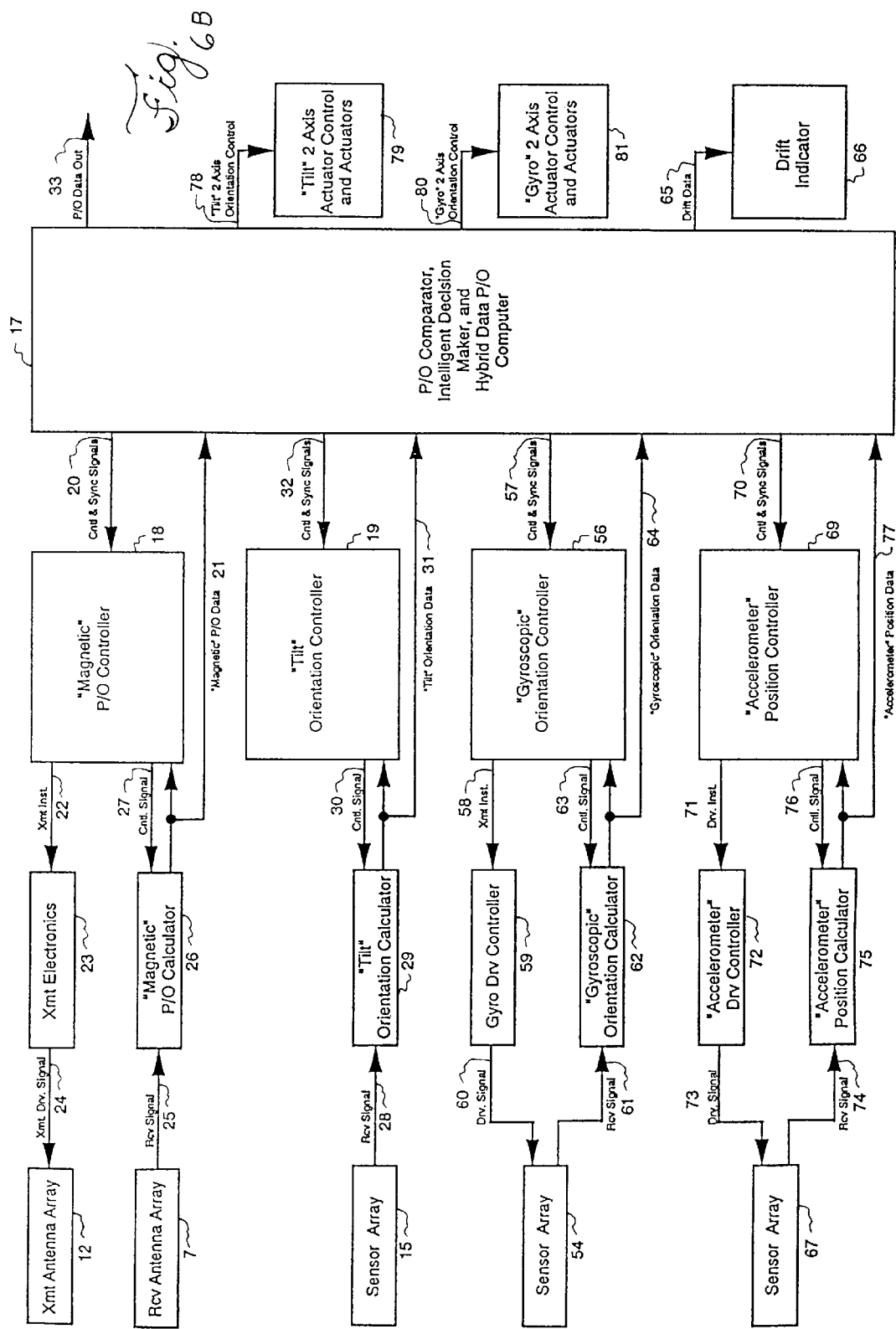

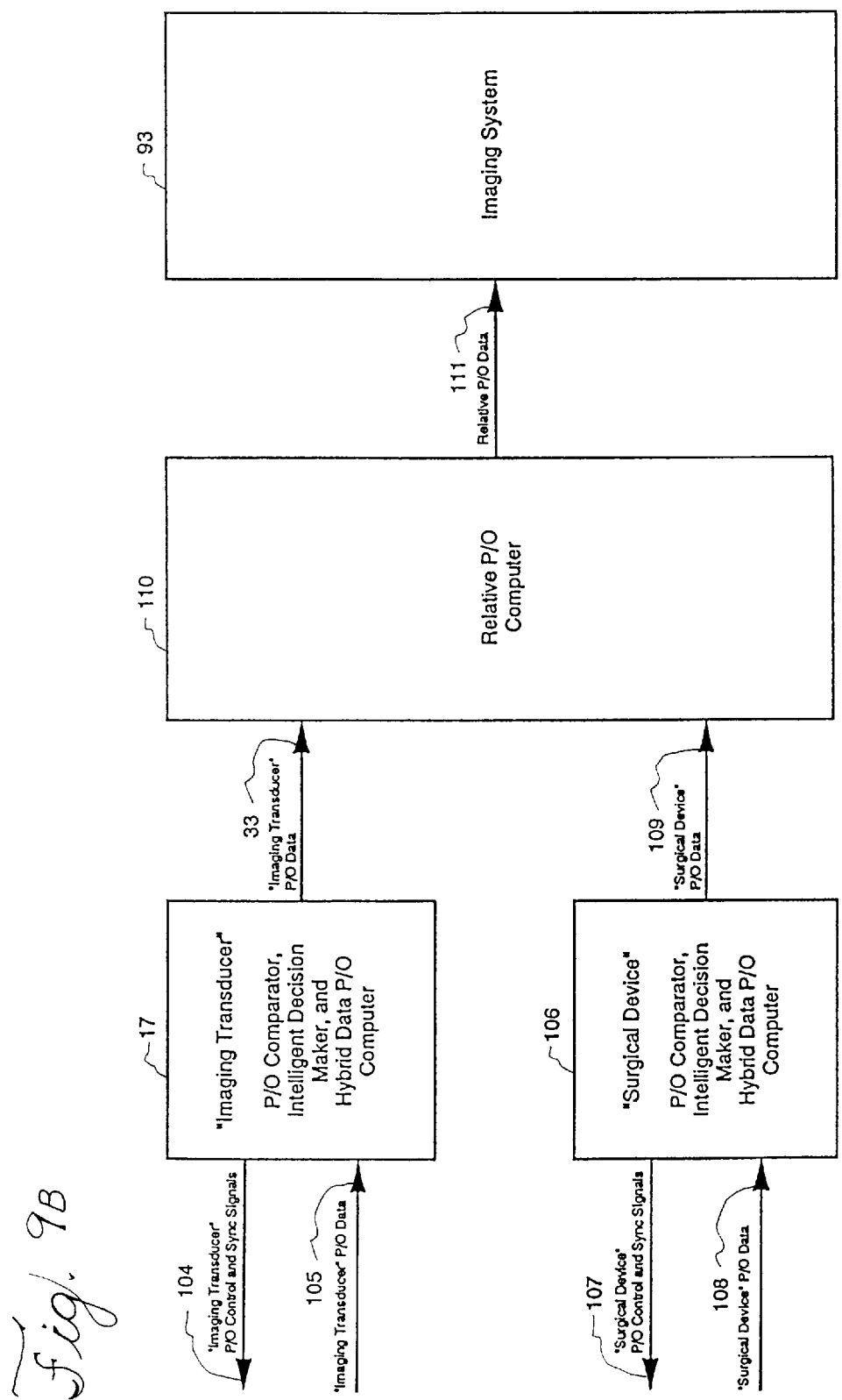

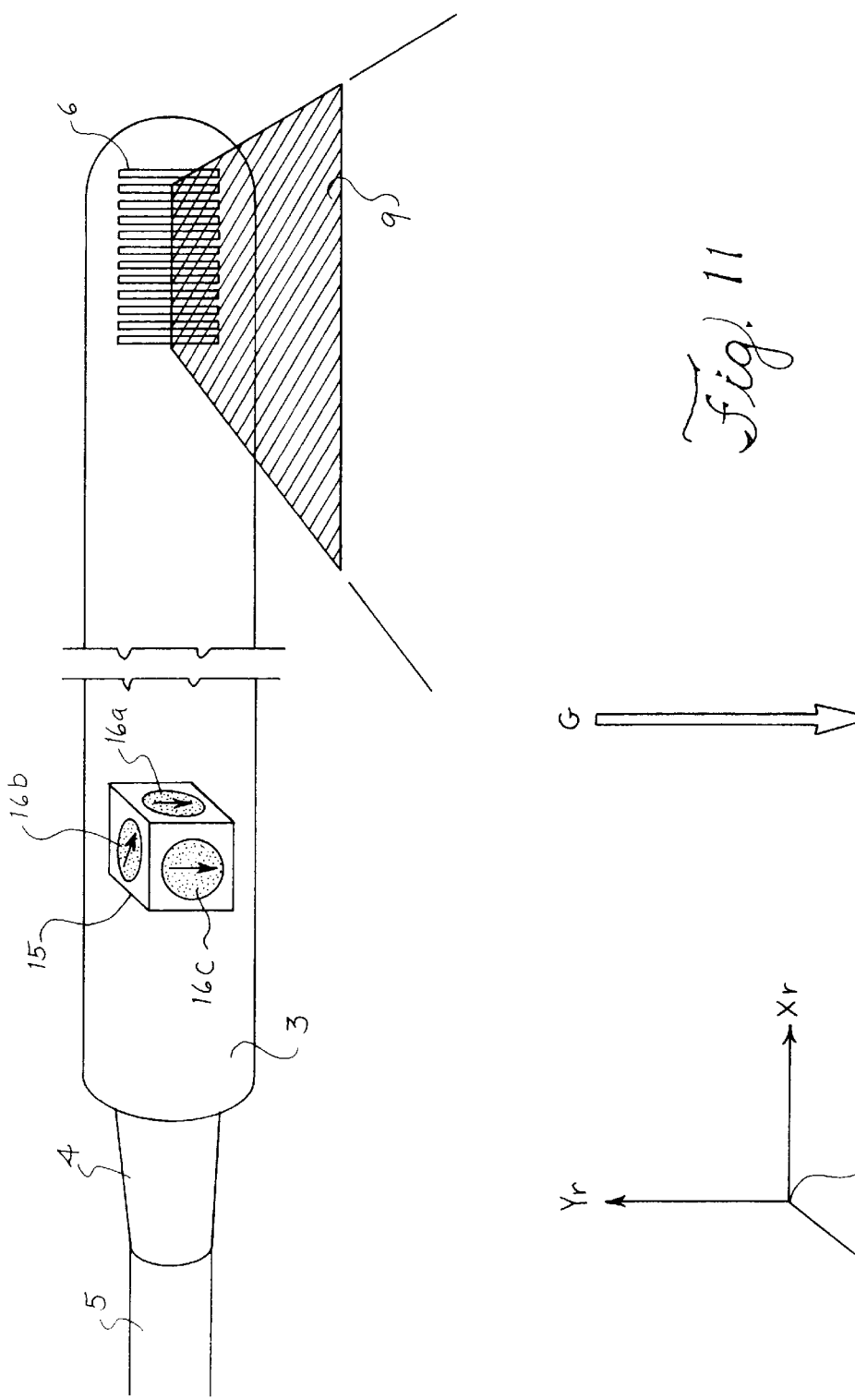

MOTION— MONITORING METHOD AND SYSTEM FOR MEDICAL DEVICES

FIELD OF THE INVENTION

The present invention provides for improved accuracy and reliability in the spatial tracking of medical devices particularly for, but not limited to, medical implements which are to be manipulated in a freehand manner. Spatial tracking refers to the measurement of at least one spatial parameter relating to the implement for the purpose of determining at least one aspect of position and/or orientation of the tracked implement. Reliability refers to the avoidance of the loss of such tracking ability due to equipment failure or the significant degradation of such tracking capability due to interferences with the motion-sensing devices utilized. The present invention further provides for the spatial tracking of relative motion between two or more medical devices wherein each of the devices has one of the tracking systems described herein. In addition, the detection of relative motion between two or more points within any non-rigid medical device, such as a flexible biopsy needle is provided.

BACKGROUND OF THE INVENTION

Medical spatial tracking is needed, for example, in order to perform three dimensional ultrasound imaging using existing medical ultrasound transducers designed for 2D imaging and, in the near future, for spatially tracking the motion of virtual-reality guided surgical tools.

As those skilled in the art of three-dimensional motion tracking are aware, one may utilize any convenient coordinate system to perform spatial (position and orientation, i.e. "P/O") tracking. Commonly used coordinate systems are Cartesian, spherical and cylindrical coordinate systems, for example.

Ultrasound, or sonography, continues to be one of the most cost-effective medical imaging modalities. Some of the reasons for this include: 1) the exam cost is comparatively inexpensive, typically a few hundred dollars, and is quickly executed, 2) the information is available in real-time, 3) the image quality and image frame rate continue to improve, 4) new modalities are appearing such as power or Color Doppler-Energy (CDE) which allow for the viewing of previously unseen phenomenon such as very low flow, 5) the array of available transducers for external, endocavity and intraoperative applications is growing, and 6) the operator interface, as supported by software and improved displays, remains relatively simple despite the vastly improved system capabilities.

Virtually all medical ultrasound imaging is two dimensional in nature wherein only the real-time or recorded two dimensional scanplane slices are viewed. It is now generally recognized that without three-dimensional ultrasound, important information and spatial relationships in the pathology may be missed in some organs such as in the heart. Thus there is growing interest in 3D ultrasound.

Other imaging modalities such as MRI and CAT scan, have long presented three-dimensional views of the body interior to the practitioner. In many cases these three-dimensional views are actually sets of stepped two-dimensional image planes or slices each situated closely adjacent to each other. The stepping is typically orthogonal to the plane of the individual two-dimensional images. The sets of stepped planes may be presented in a pseudo-3D or 3D display wherein the observer appreciates the depth-dimension information as well as the in-plane information. By timing the gathering of these image planes with the heartbeat one may even present a dynamic time-varying 3D view of the body. This is referred to as 4D imaging wherein the fourth dimension is time.

It is increasingly apparent that analogous 3D or 4D ultrasound imagery would give the medical practitioner the best possible perspective for diagnosis (and therapies) and that, if properly implemented, would allow for a wider range of sonographers having different skill levels to all get "ideal" images. In particular, if a sonographer could take a standardized volumetric (3D) image of a patient and then a doctor or expert-software program could manipulate that volumetric image data to obtain the particular desired image slice(s) of interest, or make a particular quantitative diagnostic conclusion, then the transducer probe mechanical-handling and anatomy interpretation skills required to intelligently use today's 2D ultrasound imaging hardware could be relaxed.

A significant difference between medical ultrasound equipment and MRI or CAT scan equipment is that for ultrasound, the determination of which scanline or image slice is being sampled at a particular time depends on how the sonographer is manually holding and/or moving the transducer probe relative to the patient. In virtually all current ultrasound exams the transducer probe is held in a free-hand manner so that successively sampled scanlines or image planes may easily be angulated and/or rotated in space relative to each other due to purposeful and/or unintentional hand motion of the operator. In order to provide 3D or 4D ultrasound imagery from which image features may be quantified, one needs to at least accurately know how the multiple scanlines or image planes making up a volumetric sample are spatially and temporally related to each other. One may further need to know the spatial relationship of the set of scanlines or images to certain body markers or reference points on or in the patient. Without accurate spatial address information tagged to the individual scanlines or image slices one cannot hope to construct an undistorted volumetric 3D representation of the patients tissues from multiple such scanlines or image planes. In CAT scan and MRI, for example, all scanning and scanning motions are reproducibly machine-controlled and this problem does not arise.

A variety of mechanisms have been disclosed which attempt to do with ultrasound what has already been done with MRI and CAT scan in terms of mounting the single image-plane transducer probe on a compact rotatable or slideable, i.e., translatable track, sled or helix which achieves the required translational or rotational volumetric sweeping of the 2D ultrasound image plane to get a 3D volumetric database. Although for some applications this may be workable, for most applications wherein scanning over an extended curvilinear and compliant tissue surface is required, it is not. U.S. Pat. No. 5,159,931 discloses one situation where this probably is an acceptable solution for imaging the heart through the chest wall wherein a transducer probe is utilized which is cylindrical in shape and the transducer probe is rotated, not translated, about its central axis as it looks into the body. A cone-shaped 3D volume is thus swept out via stepped angular incrementing of the 2D array around the rotation axis passing through it. The rotation axis extends into the patient's body and represents the long gripped axis of the transducer probe case. Ideally, but not necessarily, the rotating transducer probe is isolated from the skin surface by a stationary sealed acoustic window.

However, for the more general 3D applications wherein it would be desirable to move the transducer probe in a freehand, unaided manner, or at least in a minimally encumbered manner various types of sensors have been used. Some devices use accelerometers. See U.S. Pat. No. 5,353,354. Others use magnetic sensors. See U.S. Pat. No. 5,505,204; Leotta D., et al., "Three-dimensional ultrasound Imaging Using Multiple Magnetic Tracking Systems and Miniature Magnetic Sensors," proceedings of the 1995 IEEE Ultrasonics Symposium, pp. 1415–1418 (November 1995); and Detmer, P. et al., "3D Ultrasonic Image Feature Localization Based On Magnetic Scanhead Tracking: In Vitro Calibration and Validation," Ultrasound in Medicine and Biology, Vol. 20, No. 9, pp. 923–936 (1994). Still others use gyroscopes. See Shinozuka, N. et al. "Transvaginal Sonographic and Orientation Detection System Using Ceramic Gyroscopes," Ultrasound in Medicine, Vol. 15, pp. 107–113 (1996). While this can preserve some or all of the desired freedom of motion of the ultrasound transducer probe, there remain inadequacies in each of these solutions.

In particular, there is a lack of sufficiently accurate translation and angular motion-discrimination which is important for deep ultrasound imaging and for narrow-elevation, i.e., thin slice imaging in 3D. Magnetic sensors are significantly inferior in angle measurement. So are accelerometers by themselves. Gyroscopes by themselves cannot detect translations.

In addition, spatial reporting errors are caused by passive metallic or magnetic objects in the motion space when using magnetic solutions such as that disclosed in U.S. Pat. No. 5,465,724. Also, failure or degradation of a magnetic tracking system's performance may be caused by active electromagnetic interference as from an electrocautery knife, an RF ablation tool or the imaging transducer itself or from passive interference as from an associated metallic biopsy needle device.

Existing transducers incorporate in their construction undesirable magnetic materials causing "passive" interference with such magnetic position sensing systems. They also incorporate metallic, electrically conductive components arranged in a way that invite errors in magnetic tracking systems due to induced eddy currents and their companion "active" interference. Existing transducers also lack the necessary shielding so as to allow an on-board magnetic sensor to operate without significant interference from the functioning transducer itself These issues have been addressed in U.S. Pat. No. 5,465,724, Sliwa, et al.

It is thus desirable to provide a position and orientation system wherein the measurement of orientation is insensitive to electromagnetic noise and which is more accurate than known systems already described. In addition, it is desirable to provide a position and orientation system that is able to directly measure absolute orientation instead of deducing relative orientation and to measure absolute orientation with a high degree of accuracy.

Further, it is desirable to provide a position and orientation system that does not incorporate into its construction undesirable magnetic materials which cause passive interference with the position and orientation system. It is desirable to avoid inducing errors in magnetic tracking systems due to induced eddy currents in metallic, electrically conductive components and the resulting active interference. It is desirable to provide a position and orientation system having features of redundancy and, in some cases, self-optimization, self-calibration and self-testing. It is also desirable to provide a position and orientation system which can correct for electromagnetic field disturbances coming from outside the transducer probe.

It is also desirable to provide a position and orientation system that can calculate the relative position and orientation of two devices. Further, it is desirable to provide a position and orientation system that determines the relative position and orientation of points within a medical device, such as a needle, when the device cannot be made rigid or when it is impractical or undesirable to make to device rigid.

BRIEF DESCRIPTION OF THE DRAWINGS

In describing the invention and its various embodiments we shall refer to the following figures in which like item numbers refer to like items.

FIG. 6B illustrates a block diagram of a hybrid positioning system for the ultrasound system shown in FIG. 6A.

FIG. 9B illustrates a block diagram of a hybrid positioning system for the ultrasound system shown in FIG. 9A.

FIG. 11 illustrates an eighth preferred embodiment of the present invention by introducing use of tilt sensors alone for orientation sensing in an ultrasound transducer probe for endorectal applications.

SUMMARY OF THE INVENTION

Figure 1A:
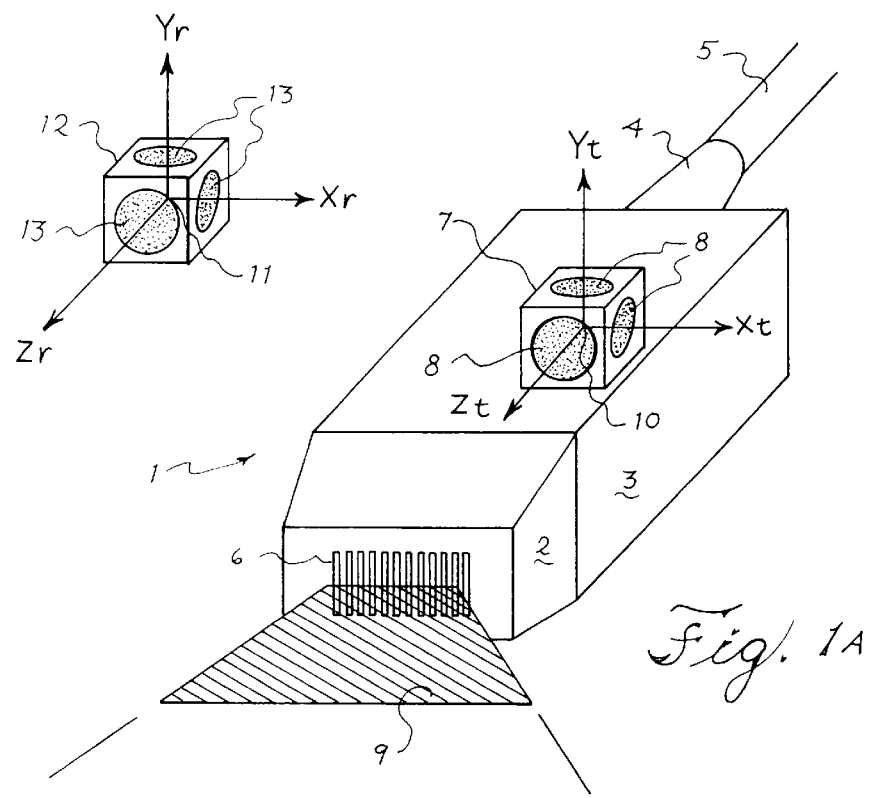
FIG. 1A illustrates a prior art medical ultrasound transducer probe utilizing a spatial magnetic positioning system.

According to a first aspect of the present invention, a movable medical imaging device having sensors for measuring the position and orientation of the movable device is provided. The device includes a first sensor disposed on the movable device for measuring a first parameter of motion and a second sensor of a different type than said first sensor disposed on the movable device. The second sensor measures a second parameter of motion that is different from the first parameter of motion.

According to a second aspect of the present invention, a system for tracking the position and orientation of a movable medical imaging device is provided. The system includes a first sensor disposed on the movable device which measures a first parameter of motion and a second sensor, of a different type than said first sensor, disposed on the movable device which measures a second parameter of motion. A transmit array is located remotely from the movable device and a computer is coupled to the transmit array, the first sensor and the second sensor. The computer instructs the transmit array to transmit signals that are received by the first sensor and the computer receives signals from the first sensor indicative of the first parameter of motion and from the second sensor indicative of the second parameter of motion.

According to a third aspect of the present invention a position and orientation system for tracking partial parameters of a medical implement is provided. The system includes a first subsystem disposed on the medical implement having a sensor of a first type for measuring at least one degree of freedom of the medical implement a second subsystem disposed on the medical implement having a sensor of a second type that is different from the sensor of the first type for measuring at least one degree of freedom of the medical implement.

According to a fourth aspect of the present invention, a position and orientation system for tracking the relative position of a medical implement with respect to a medical imaging device is provided. The system includes a first subsystem disposed on the medical implement for measuring at least one degree of freedom of the medical implement, a second subsystem, different from the first subsystem, disposed on the medical implement for measuring at least one degree of freedom of the medical implement, a third subsystem disposed on the medical imaging device for measuring at least one degree of freedom of the medical imaging device, and a fourth subsystem, different from the third subsystem, disposed on the medical imaging device for measuring at least one degree of freedom of the medical imaging device. A computer coupled to the first, second, third and fourth subsystems receives measured signals from the first, second, third and fourth subsystems and computes the relative position of the medical implement with respect to the medical imaging device.

According to a fifth aspect of the present invention a system for determining the relative position of a point on a deformable device with respect to another point on the device is provided. The system includes a first sensor disposed on the deformable device for measuring distortions of the device, a computer coupled to the sensor for receiving the measured distortions and computing relative position and orientation, and an imaging system coupled to the computer for displaying the deformable device wherein the imaging system receives the relative position and orientation data and reflects changes in relative position and orientation data on a display.

According to a sixth aspect of the present invention, a method of tracking the position and orientation of a movable device is provided. The method includes the steps of providing a first sensor disposed on the movable device, providing a second sensor, of a different type than the first sensor, disposed on the movable device measuring a first parameter of motion with the first sensor, and measuring a second parameter of motion with the second sensor.

DESCRIPTION OF THE PRESENTLY PREFERRED EMBODIEMENTS

FIG. 1A illustrates a prior art medical ultrasound transducer probe utilizing a spatial magnetic positioning system. The medical ultrasound transducer probe 1 includes a nosepiece 2, a case 3, a cable strain-relief 4, and a cable 5. Inside the nosepiece 2 can be seen an acoustic phased array 6. The phased array 6 is shown emanating (or receiving) ultrasound energy over a two dimensional image slice 9. It is nosepiece 2 and its contained array 6 that are placed directly on the tissue (not shown) to be scanned. Inside transducer probe 1, and more particularly, in this example, inside case 3, is also shown a spatial magnetic position sensor 7. The position sensor 7 consists of three orthogonally arranged sensing coils or magnetic fluxgates 8.

A spatial coordinate system 10 is shown in the transducer probe 1 having Cartesian coordinate axes $X_t$, $Y_t$, and $Z_t$ wherein the subscript "t" designation indicates "transducer probe". This coordinate system is that of the movable transducer probe thus it maintains its position and orientation ("P/O") relative to transducer probe 1 and is representative of the P/O of transducer probe 1. It will also be recognized that since the scan plane 9 maintains a constant P/O relative to transducer probe 1 (in this example), that coordinate system 10 is also representative of the P/O of scan plane 9. Although one can see that sensor 7 is displaced or offset from scan plane 9, that offset is fixed and may be easily accounted for. Thus the P/O of magnetic sensor 7 is also that of scan plane 9 by easily taking into account the fixed offset.

Another coordinate reference system 11 having coordinates and axes $X_r$, $Y_r$, and $Z_r$, wherein the subscript "r" indicates "reference" is preferably fixed relative to the transducer probe 1. In this example, the reference system 11 is fixed relative to the examination room. Thus any motion of the transducer probe 1 on the patient will result in sensor 7 being able to report the P/O of the transducer probe 1 (and its scan plane 9) relative to the stationary examination room and its reference system 11. Since the sensor can report scan plane's 9 P/O, one may associate each such spatial address of scan plan 9 with each such sampled scan plane 9 such that the spatial relationships of multiple associated scan planes may be known and recorded.

A brief explanation of how magnetic spatial sensors work is now in order. The stationary 3-coil magnetic field transmitter 12 is placed in the examination room, for example, at the origin of coordinate system 11. Each of the three transmitter coils 13 is current-pulsed in sequence, each of the three coils emitting a magnetic dipole field oriented to its own coil, the three fields thus also being orthogonal to each other as are the coils. The sensed currents induced in sensor 7 are sampled on each of the three sensing coils 8 as each transmitting coil is energized. In this manner three orthogonal measurements are made at sensor 7 of each of the three transmitted fields. This provides an array of nine data points which may, as one of ordinary skill in the art recognizes, using matrix mathematics, be used to compute the position $X_r$, $Y_r$ and $Z_r$ and the orientation $\theta_{r,x}$, $\theta_{r,y}$, and $\theta_{r,z}$ of transducer probe 1 relative to the stationary transmitter 12. Thus, the magnetic array 7 is capable of measuring 6 degrees of freedom (DOF). As the transducer probe 1 is moved relative to the room and thus relative to the patient and the coordinate system 11, the values of the distance of transducer probe 1 from the transmitter as determined solely from $X_r$, $Y_r$ and $Z_r$ of moving sensor 7 and of the orientation of transducer probe 1 as determined by $\theta_{r,x}$, $\theta_{r,y}$, and $\theta_{r,z}$ of moving sensor 7 will dynamically change. Those familiar with vector mathematics will recognize that the three sensed field values for each transmitted field represent the vector components of the transmitted fields as viewed by the sensor 7.

Experience has shown that magnetic spatial sensor systems of the type shown in FIG. 1A and of the generic type discussed in the prior art references can be degraded or interfered with under certain circumstances. The accuracies can degrade very rapidly with conductive and magnetic objects in the magnetic field including those near the sensor and with interferences from the operating ultrasound system, the ultrasound transducer probe and any related supporting equipment. Thus it has been found that the stated performance of such systems is routinely obtainable only in an environment free of such real-world interferences.

As one of ordinary skill in the art appreciates, transmitted electromagnetic fields interact with metallic objects. Specifically, a metal plate or film influenced by a dynamic transmitted magnetic field, will have electrical currents induced in it. The transient electrical currents will, in turn, induce a further transient magnetic field even after the electromagnetic transmitter is turned off. The extra and undesired induced magnetic fields alter the applied field resulting in position errors. As an example, a metal gurney or metallic halogen lamp shell may cause such induced interfering magnetic fields. It will also be recognized that any permanent magnet or semipermanent magnet in the motion field will also cause magnetic fields which will be sensed as part of the transmitted magnetic field thus also resulting in position errors. Transducers are currently designed in a manner wherein such passive transient interferences are affecting magnetic positioners.

It will further be recognized that if transducer probe 1 is operating in a manner to produce an image 9 it may well emit electromagnetic fields which also couple into sensor 7 resulting in further position errors. The same applies to any electromagnetic device in or near the patient and transducer probe 1, such as an electrocautery knife or a metallic trocar or forceps, for example. Thus although magnetic positioning systems are truly elegant in concept they are presently limited in their performance due to a variety of such interactions.

Figure 1B:
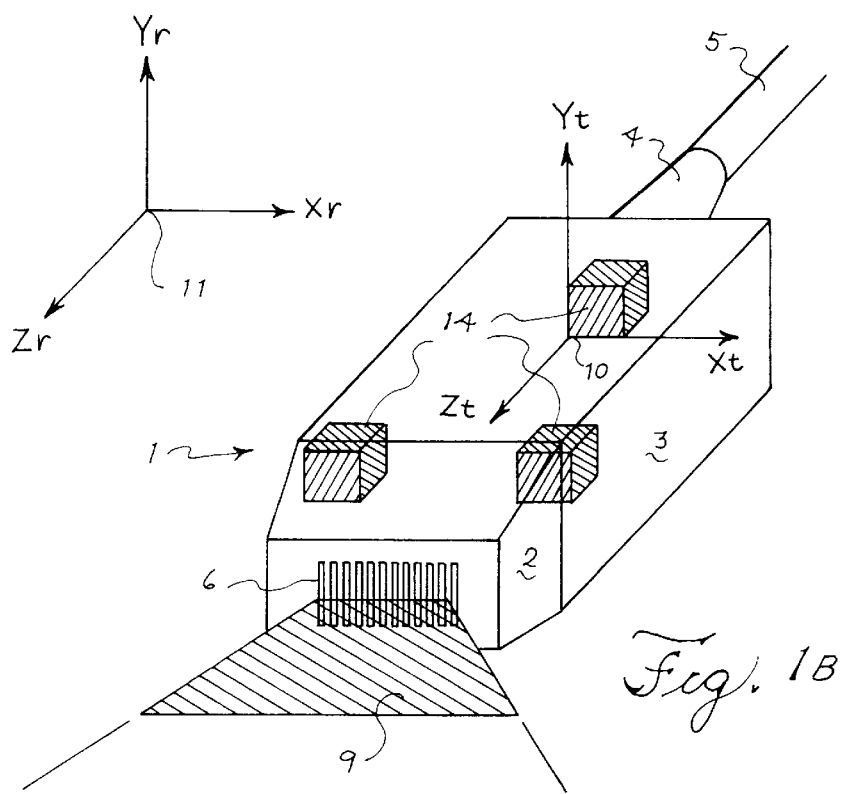
FIG. 1B illustrates a prior art medical ultrasound transducer probe utilizing a set of accelerometers for reporting spatial position.

FIG. 1B illustrates a prior art medical ultrasound transducer probe utilizing a set of accelerometers for reporting spatial position. This prior art transducer probe 1 has a different sensor arrangement from that of FIG. 1A. Three accelerometers 14 are placed at three positions within the case 3 of the transducer probe 1 and, all three are stationary with respect to transducer probe reference system 10. An accelerometer reports the forces it senses due to the inertially induced distortion of the accelerometer 14 as such accelerations are imposed on it. For example, as transducer probe 1 is either translated or reoriented (tilted or rotated) or both on the body, the transducer probe must be accelerated. Whenever the transducer probe is accelerated thereby, changing its momentum, the change of momentum, either in translational velocity or tilting rate (angular or rotational rate) or both, may accelerate any or all of accelerometers contained in the transducer probe.

By placing multiple such accelerometers 14 in case 3 one tries to ensure that regardless of what translational or angular accelerations are taking place that at least one accelerometer is situated such that it may sense that acceleration. It will be recognized that any of the three accelerometers 14 of FIG. 1B will equally sense a pure translational acceleration of transducer probe 1. But it will also be recognized that for an angular twisting or rotational acceleration of transducer probe 1, say about axis $Z_t$, only accelerometers displaced from axis $Z_t$ will sense that acceleration if accelerometers 14 are designed to sense translational acceleration (as opposed to angular acceleration). As ultrasonic transducer probes of the type 1 get smaller and smaller with progressing technology one is unable to arrange for translational accelerometers to be located far from axis $Z_t$. Thus such translational accelerometers of the prior art become increasingly less sensitive in smaller transducer probes if they are used to sense rotational accelerations. Using only rotational (angular) accelerometers will solve this problem but will cause the same problem with respect to the sensing of translational accelerations if those need to be sensed. The prior art is subject to these unacceptable tradeoffs.

Finally, since accelerometers sense acceleration they deduce distance using a double integration technique. Acceleration is integrated to velocity and velocity is integrated to position. It will be obvious to those familiar with physics that one must assume an initial position and an initial velocity or must arbitrarily define the initial position and velocity at the start of transducer probe 1 motion. This only indicates where the transducer probe has moved to relative to its starting point, i.e., when the probe started sensing accelerations, and not relative to a stationary external reference system.

Thus for the prior art accelerometer solution wherein translational accelerometers are utilized to measure both translational and angular accelerations and double integration is utilized to deduce position and angle changes the system is subject to substantial inaccuracies. Using such a system does not allow the determination of absolute position. If the transducer probe motion involves fine angular control one will be at a fundamental disadvantage with such a prior art system incapable of sensing absolute angle directly or subtle angular rate changes directly. Numerous applications will require the need to return to a previous scan position as, for example, an image plane of interest seen in a set of previously gathered images. Since accelerometers alone can not indicate absolute position they are subject to drift errors making such a return to an original position and orientation impossible after extended motions.

Figure 2A:
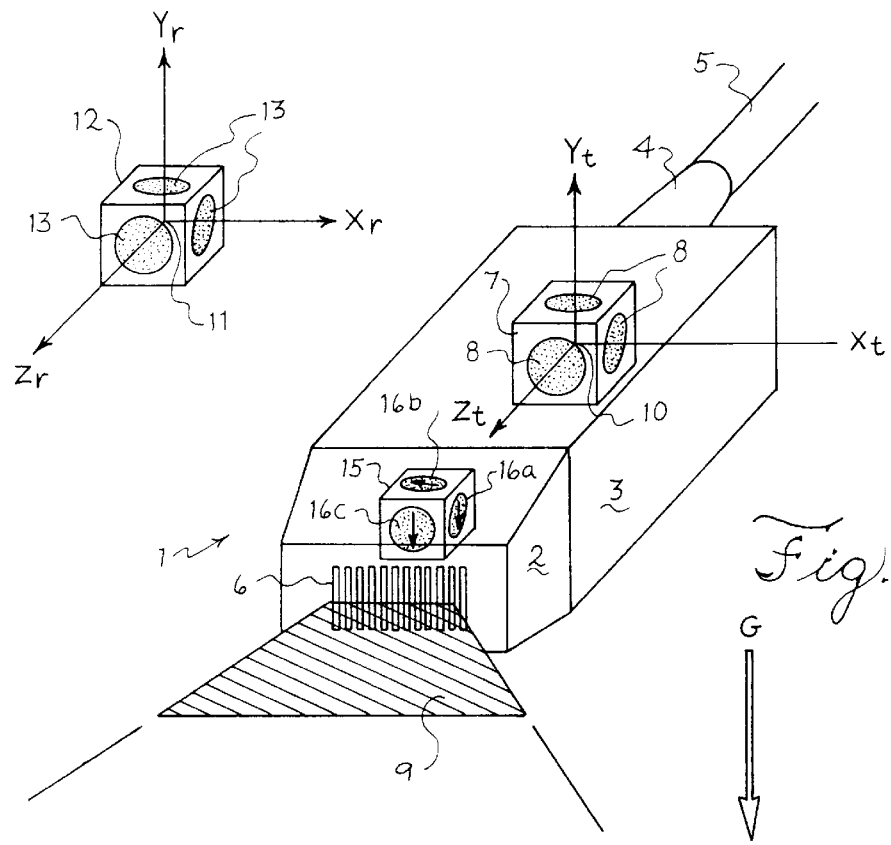
FIG. 2A illustrates a medical ultrasound transducer probe containing a hybrid position and orientation system according to a first preferred embodiment of the present invention.

FIG. 2A illustrates a medical ultrasound transducer probe containing a hybrid position system according to a first preferred embodiment of the present invention. The first preferred embodiment of the present invention provides spatial relationship information for 3D ultrasound-imaging with unparalleled accuracy by utilizing a hybrid-technology positioner and an associated algorithm designed for such a hybrid positioner. The transducer probe 1 includes a hybrid positioning system housed therein. In this preferred embodiment the hybrid positioning system includes a magnetic spatial positioner 7 in combination with an additional and complimentary multiaxis tilt (i.e., inclination or angle) sensor 15. Multiaxis tilt sensor 15 is schematically indicated as having three orthogonal single axis tilt sensors 16$a,b,c$ capable of reporting the angular orientation of transducer probe 1 relative to gravity vector G. In the transducer probe's shown orientation with respect to gravity vector G, tilt sensors 16$a$ and 16$c$ will be able to sense the gravity vector (as indicated) whereas tilt sensor 16$b$, being perpendicular to the gravity vector, is temporarily unable to sense any component of gravity vector G. Obviously, gravity vector G will not always be perpendicular to one of the three tilt sensors, but even so, rotations about an axis parallel to G cannot be measured by tilt sensors 16$a,b,c$. Equally obvious is that when sensor 15 is in an orientation where none of the tilt sensors are perpendicular to gravity vector G, the orientation with respect to gravity is sensed by all three tilt sensors 16$a,b,c$. Tilt sensors 16$a,b,c$ need not necessarily be orthogonally constructed, as depicted, to function properly. The present invention is not, however, limited to any particular choice of coordinate system or choice of spatial parameter(s). The coordinate system itself may be stationary or may even be moving. In addition, while the present invention is discussed with reference to medical ultrasound imaging devices used for three dimensional (3D) ultrasound imaging, the present invention is not so limited.

In a preferred embodiment the Fredericks Company, 2400 Philmont Ave., P.O. Box 67, Huntingdon Valley, Pa., 19006-0067, provides single and dual axis tilt sensors which utilize an electrolytic liquid. The encapsulated pool of electrolytic liquid is penetrated by electrodes capable of sensing the changing length of the electrode which is wetted by the shifting conductive electrolytic liquid. In this manner, if the electrodes are attached to a container containing the electrolytic liquid, then the electrical resistance measured through each such electrode and the shifting liquid surface can be used to deduce the orientation of the liquid container (the sensor) relative to gravity. Such electrolytic sensors are widely used on modern aircraft and surveying equipment.

An advantage of such tilt sensors is that they are inexpensive, come in very small sizes and require a simple and compact interface circuit board. Their performance is not dependent on the size of the transducer probe nor where in the transducer probe they are positioned or packaged. Their angular resolutions are on the order of about 0.020 to about 0.002 degrees (depending on the model of sensor) which is at least an order of magnitude better than that of a magnetic spatial positioner (approx. 0.2–0.5 degrees) in a very carefully constructed real-world use wherein the transducer probe 1 may be one to three feet from the magnetic transmitter and there are minimal amounts of metal and electromagnetic interference present. With metallic or electromagnetic interference, as discussed, the magnetic sensor performance rapidly degrades from these values. In a preferred embodiment the Fredericks series 0728 with a 360 degree operating range, 0.0017 degree angular resolution, and null repeatability of 0.05 degrees are well suited for this application. Suitable tilt sensors are also available from Spectron Inc. of Hauppauge, N.Y. Spectron provides single, dual and triple axis tilt sensors. The Spectron SSY0090C with a plus/minus 45 degree range is temperature compensated and utilizes CMOS electronics. The standard non-CMOS models SSY0090 and SSY0091 provide a resolution of 0.005 degrees.

In 3D imaging applications wherein one desires to image deep tissues and/or one desires to utilize a transducer probe 1 with a very thin image plane 9 there is a requirement for very fine angular tracking of the image plane 9. Ideally one would like to be able to sample image planes 9 closely juxtaposed to each other thus sampling the entire volume of tissue. In an application wherein such planes are swept out volumetrically primarily by a tilting of transducer probe 1 on the tissue, one needs very fine angular sensing of that tilt motion to ensure that the image planes are properly spaced (or even slightly overlapped if desired) at depth. As the image plane 9 slice thickness decreases the angular control required is even tighter. Tilt sensors of the type described are best able to do this function in terms of accuracy and resistance to interference.

Figure 2B:
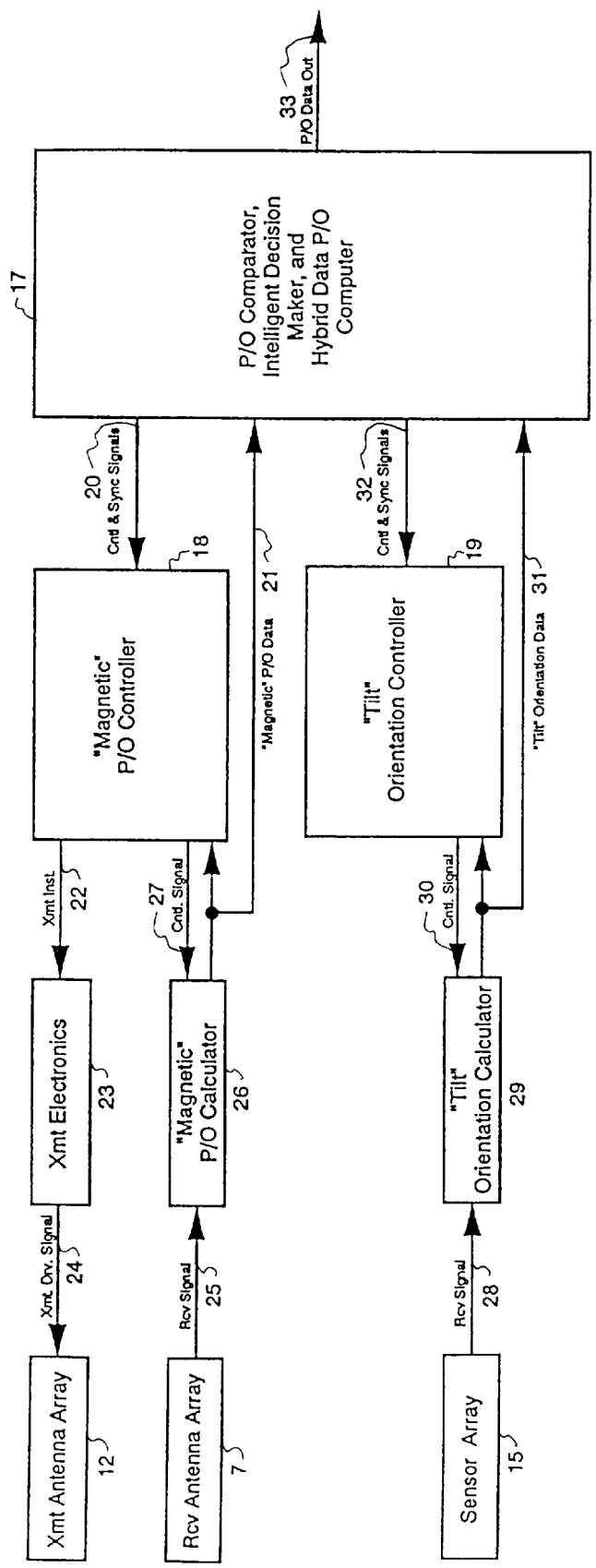
FIG. 2B illustrates a block diagram of the hybrid position and orientation system for the ultrasound system shown in FIG. 2A.

FIG. 2B illustrates a block diagram of the hybrid positioning and orientation system for the ultrasound system shown in FIG. 2A. The hybrid position and orientation system includes the transmit antenna array 12, the receive antenna array 7 and the sensor array 15 as shown in FIG. 2A. Also included are a P/O comparator, intelligent decision maker and hybrid data P/O computer 17, a magnetic P/O controller 18, a tilt P/O controller 19, transmit electronics 23, a magnetic P/O calculator 26 and a tilt orientation calculator 29. Primary control of this system is the responsibility of the P/O comparator, intelligent decision maker, and hybrid data P/O computer 17 that receives input from and controls the magnetic P/O controller 18 and tilt orientation controller 19. It also provides output of the computed P/O data 33 to the ultrasound imaging system (not shown) and receives instructions from the ultrasound imaging system via system control signals 128.

On the top half of FIG. 2A is the magnetic P/O subsystem. The magnetic P/O subsystem is an active device. Magnetic P/O controller 18 generates and sends transmit instructions 22 and control signals 27 to the transmit electronics 23 and magnetic P/O calculator 26 respectively, in accordance with control, data, and synchronization signals 20. Transmit electronics 23 generate and apply the transmit drive signal 24 to the transmit antenna array 12. The signals transmitted by the transmit array 12 are detected with receiver array 7 where they are converted to receive signal 25 and sent to the magnetic P/O calculator 26. The magnetic P/O calculator computes the magnetic subsystem sensed P/O data 21 and sends the data to both the magnetic P/O controller 18, where they are used in the feedback control of the subsystem, and P/O comparator, intelligent decision maker, and hybrid data P/O computer 17.

On the bottom half of FIG. 2A is the tilt P/O subsystem. The tilt P/O subsystem is a passive device and lacks the equivalent of a transmit side as shown with the magnetic P/O subsystem. Synchronization with the magnetic subsystem may be required and can be supplied by control, data, and synchronization signals 32. Tilt sensor array 15 generates a receive signal 28 for each tilt sensor in the array, that is proportional to each tilt sensors alignment with the gravitational field vector G and forwards the receive signal to the tilt orientation calculator 29. The tilt orientation calculator 29 computes orientation data 31 and sends the data to both the tilt orientation controller 19, where the data is used in the feedback control of the system, and the P/O comparator, intelligent decision maker, and hybrid data P/O computer 17.

The P/O comparator, intelligent decision maker, and hybrid data P/O computer 17 may do any one of the following with the data it receives from the magnetic P/O controller in the form of magnetic P/O data 21 and from the tilt orientation controller 19 in the form of tilt orientation data 31: (1) it may pass the data from the subsystem pre-selected for each P/O parameter directly to the output 33; (2) it may decide which subsystem is to supply data to the output for each P/O parameter based on a predetermined set of rules and on the current values of the data 21 & 31, for example, it may use tilt sensor data from tilt sensors in valid tilt sensor orientations and then switch to use of magnetic data for orientations about the earth's gravitational vector G; (3) it may determine that a sensor, some sensors, or a subsystem has failed and automatically switch to using data from a sensor, sensors, and/or subsystem that it knows is producing reliable data; and (4) it may accept the data from each subsystem, either in the form of pre-computed P/O data, raw sensor data, and/or any appropriate intermediate data format, and compute enhanced P/O estimates based on intelligent use of all data available from the subsystems and then send the re-computed P/O data 33 to the output. In addition, the computer 17 can arrange for the sharing of data between the subsystems and allow the controllers 18 and 19 for each subsystem to make refined computations using data from another subsystem.

Figure 3A:
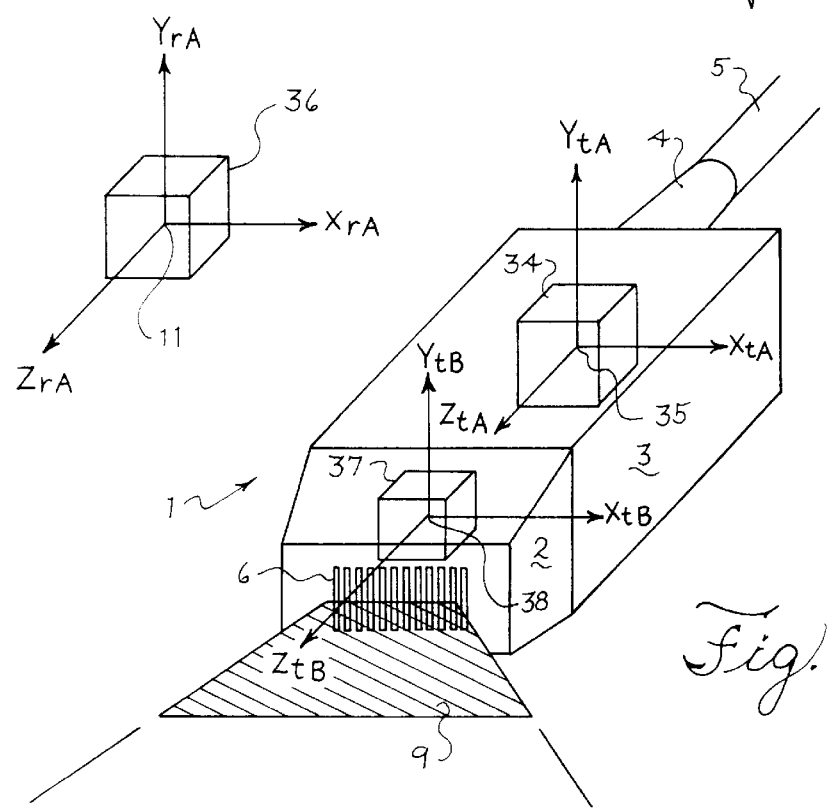
FIG. 3A illustrates a medical ultrasound transducer probe containing one active position and orientation subsystem and one passive position and orientation subsystem according to a second preferred embodiment of the present invention.

FIG. 3A illustrates a medical ultrasound transducer probe containing one active P/O subsystem and one passive P/O subsystem according to a second preferred embodiment of the present invention. The active subsystem consists of transmitter array 36, shown aligned with the reference coordinate system 11, and receiver array 34 shown aligned with transducer probe coordinate system 35. The passive subsystem consists of receiver array 37 located at transducer probe coordinate system 38. Importantly both receiver arrays are contained in the same rigid transducer probe case 3 such that they experience the same relative translations and rotations as transducer probe 1 is moved, typically by the sonographer.

Figure 3B:
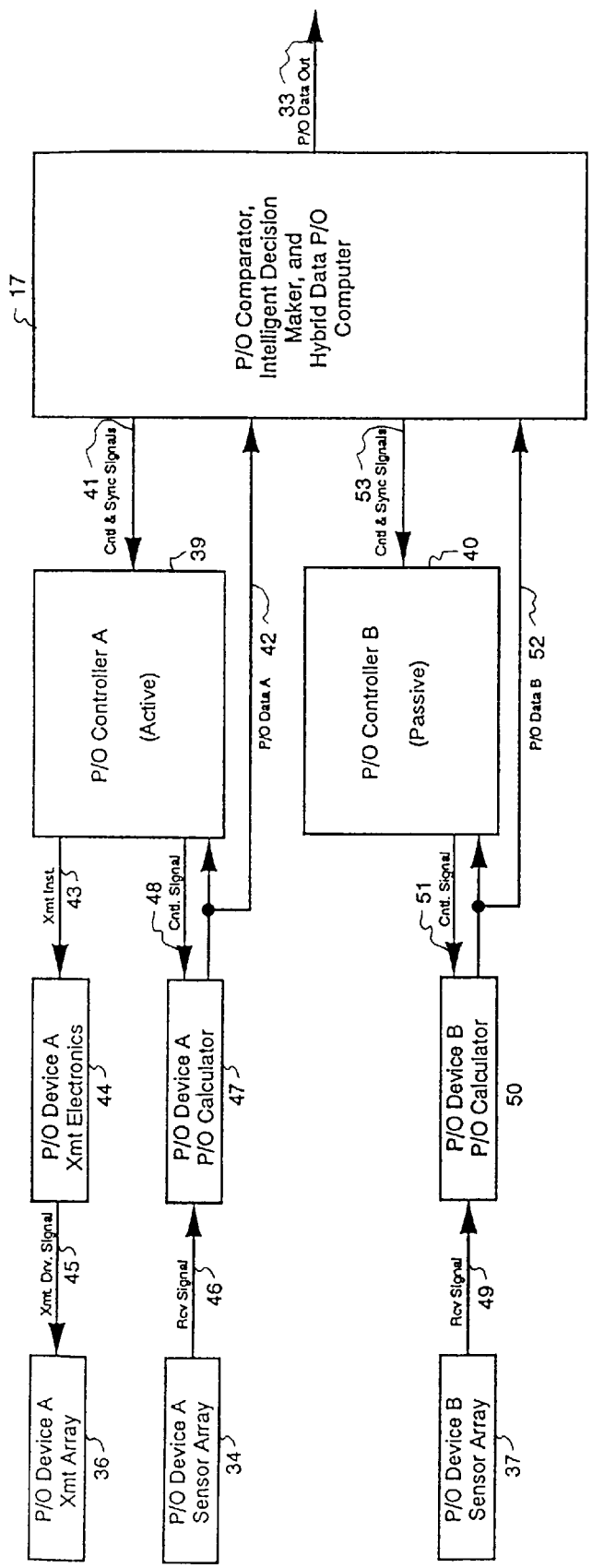
FIG. 3B illustrates a block diagram of the hybrid position and orientation system for the ultrasound system shown in FIG. 3A.

FIG. 3B illustrates a block diagram of a hybrid P/O system containing the active and passive subsystems FIG. 3A. The preferred embodiment shown in FIGS. 3A and 3B is a generalization of the specific embodiment shown in FIGS. 2A and 2B where the active P/O subsystem was the magnetic P/O subsystem and the passive P/O subsystem was the tilt P/O subsystem. Primary control of this system is the responsibility of the P/O comparator, intelligent decision maker, and hybrid data P/O computer 17 that receives input from and controls P/O controller(A) 39 (for the active device) and P/O controller(B) 40 (for the passive device). It also provides output of the computed P/O data 33 to the ultrasound imaging system (not shown). P/O controller(A) 39 generates and sends transmit instructions 43 and control signals 48 to the transmit electronics 44 and P/O device(A) P/O calculator 47 respectively, in accordance with control, data, and synchronization signals 41. Transmit electronics 44 generate and apply the transmit drive signal 45 to the transmit array 36. The signals transmitted by the transmit array 36 are detected with receiver array 34, where they are converted to receive signal 46 and sent to the P/O device(A) P/O calculator 47. The P/O device(A) P/O calculator computes P/O data 42 and sends the data to both P/O controller (A) 39, where they are used in the feedback control of the subsystem, and P/O comparator, intelligent decision maker, and hybrid data P/O computer 17.

P/O subsystem(B) is a passive device and lacks the equivalent of the transmit side of the active P/O subsystem. Synchronization with P/O subsystem(A) may be required and can be supplied by control, data, and synchronization signals 53. Passive sensor array 37 generates a receive signal 49, for each sensor in the array, and forwards the receive signal to P/O device(B) P/O calculator 50. P/O device(B) P/O calculator 50 computes P/O data 52 and sends the data to both P/O controller(B) 40, where it is used in the feedback control of the system, and the P/O comparator, intelligent decision maker, and hybrid data P/O computer 17. The P/O comparator, intelligent decision maker, and hybrid data P/O computer 17 may do any of the same things with the data it receives in the forms of data signals 42 & 52 as was already described with respect to FIG. 2B.

Alternatively, the ultrasound probe may have two passive subsystems or two active subsystems.

Figure 4A:
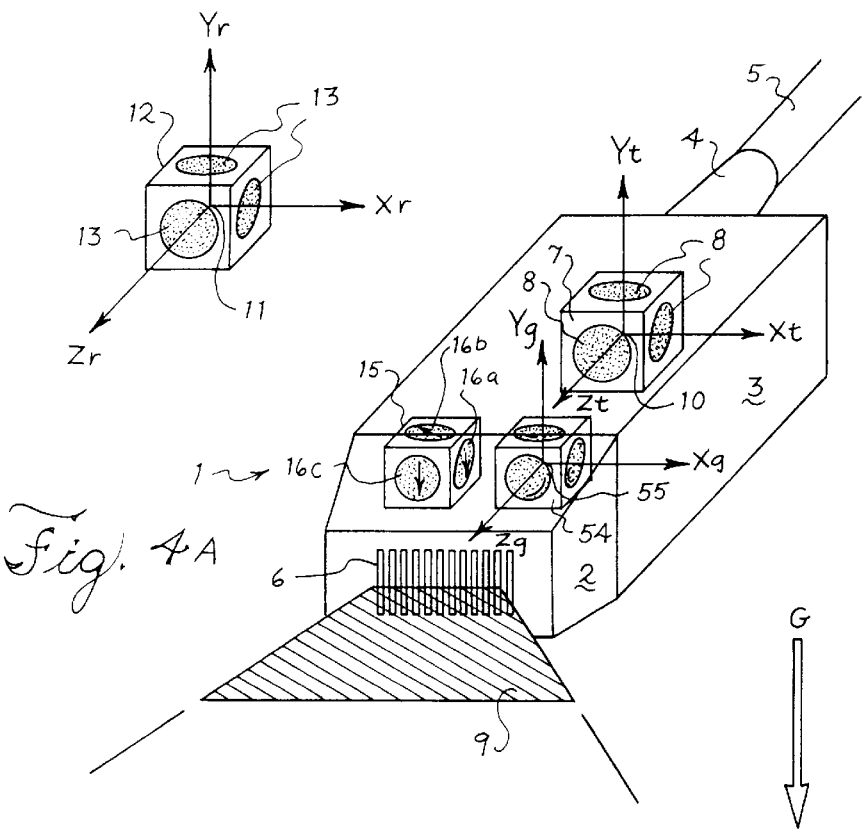
FIG. 4A illustrates a medical ultrasound transducer probe containing a hybrid positioning system which utilizes magnetic, tilt, and gyroscopic position and orientation subsystems according to a third preferred embodiment of the present invention.

FIG. 4A illustrates a transducer probe 1 similar to that shown in FIG. 2A except for the incorporation of an additional gyroscopic orientation subsystem depicted in FIG. 4A by sensor array 54. Gyroscopic sensor array 54 is schematically indicated as having three orthogonal gyroscopes capable of reporting relative angular movements of transducer probe 1. While the parallel alignment of each of the three orthogonally oriented sensors of gyroscopic array 54 with one of the three orthogonally oriented tilt sensors 16a,b,c of tilt sensor array 15 is shown, it should be clear to anyone skilled in the art that parallel alignment of the sensors is not required in order to relate 3 axis rotations of one sensor array to the other. Additionally the sensors within each array need not be orthogonal to each other. As will be described in detail hereinafter, the gyroscopic subsystem can be dynamically recalibrated using orientation data detected by the tilt subsystem.

The hybrid system shown in FIG. 4A having both a tilt orientation subsystem and gyroscopic orientation subsystem, and a means to intelligently and dynamically re-calibrate the gyroscopic subsystem detected orientation using tilt subsystem detected orientation data, is capable of yielding high accuracy orientation estimates that are not limited by the sensors' orientation to the earth's gravitational field vector G. For reasons stated during the discussion of FIG. 2A, tilt sensors are incapable of detecting rotations about G, but can provide highly accurate and absolute estimates of orientation when capable of sensing a significant component of G. Gyroscopic sensors, on the other hand, provide highly accurate sensing of rotations that are independent of the sensors alignment to G and that can be integrated to provide estimates of relative orientation. Gyroscopic orientation detectors suffer from the accumulation of sensor errors during the integration of sensor detected rotations, causing the accuracy of the orientation estimate to drift between calibrations. By intelligently determining when a gyroscopic sensor needs recalibration, and when it is sufficiently misaligned with G that tilt sensor data will be available for its recalibration, the hybrid device of this preferred embodiment of the present invention can automatically re-calibrate the gyroscopic sensors with tilt sensor data whenever the orientation of the transducer probe 1 permits.

In a preferred embodiment gyroscopic sensors of the type QRS11-00100-101 available from Systron Donner Inertial Division, 2700 System Drive of Concord, Calif. 945118-1399 which employ the Coriolis principle to induce voltage changes on specially constructed quartz oscillators may be used. These sensors have threshold resolutions of <0.004 degrees/sec and short term bias stabilities (over 100 sec) of 0.002 degrees/sec. To maintain an angular accuracy better than the 0.2 degree accuracies achievable with the better magnetic P/O systems, these gyroscopes with their 0.002 degree/sec short term bias stabilities would need to be calibrated at least once every 100 seconds. More frequent recalibration would of course lead to higher maintained angular resolution accuracies. For example, if acquisition of an entire 3D data set is completed within 10 seconds, the drift error due to integration of the output voltage of a gyroscope with a 0.002 degree/sec short term bias stability will be less than or equal to 0.02 degrees, bettering the magnetic subsystem by an order of magnitude.

To maintain absolute angular accuracies to be less than 0.2 degrees, for example, each gyroscopic sensor must be recalibrated at least every 100 seconds between 3D data set acquisitions. It is highly likely that the sonographer will, during this 100 second time interval, randomly position the transducer probe to a sufficient number of orientations to permit recalibration of each gyroscopic sensor. A display for notifying the sonographer to perform a transducer probe re-orientating procedure permitting recalibration of each gyroscopic sensor within the 100 second drift interval may be required (see drift indicator 66 of FIG. 4B) which will be described hereinafter. It is also possible to automatically re-calibrate each gyroscopic sensor by using an actuator (see actuator 79 & 81 of FIG. 6B) to automatically reorient the gyroscopic array 54 and possibly tilt sensor array 15 whenever recalibration is required which will be described hereinafter. Obviously, it is not necessary to reorient a three axis tilt sensor array since all orientations except rotations about G will be sensed by this array regardless of its orientation to G, and reorientation will not permit the tilt sensor array to sense orientations about G. Nonetheless, some implementations of the present invention are simplified, both mechanically and mathematically, if both gyroscopes and tilt sensors can be reoriented.

Figure 4B:
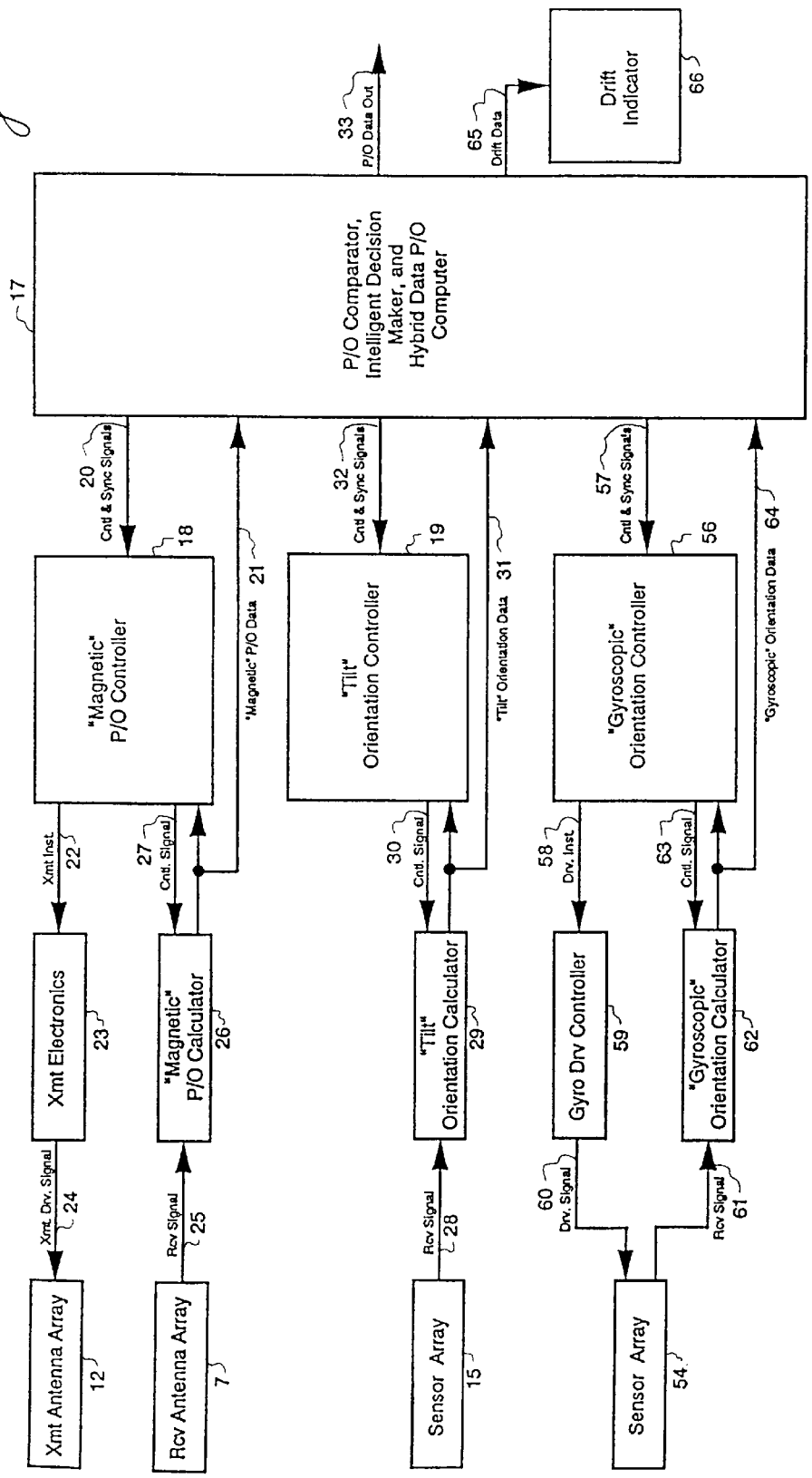
FIG. 4B illustrates a block diagram of the hybrid positioning system for the ultrasound system shown in FIG. 4A.

FIG. 4B illustrates a block diagram of the hybrid P/O system for the ultrasound system shown in FIG. 4A. The presentation of the magnetic and tilt P/O subsystems has not changed from their presentation in FIG. 2B. Added, is the control system for the gyroscopic subsystem and drift indicator 66.

The P/O comparator, intelligent decision maker, and hybrid data P/O computer 17 controls the gyroscopic orientation controller 56 by means of control, data, and synchronization signals 57. The gyroscopic orientation controller 56 generates and sends drive instructions 58 to the gyroscopic drive controller 59 and control signal 63 to gyroscopic orientation calculator 62. Gyroscopic drive controller 59 applies a drive signal 60 to the gyroscopic sensor array 54. Rotations are sensed by the array and converted to receive signal 61 and sent to the gyroscopic orientation calculator 62 that performs the integration process necessary to convert signal 61 into relative orientation estimates. The computed gyroscopic orientation data 64 is applied to the gyroscopic orientation controller 56, where it is used in the feedback control of the subsystem, and to P/O comparator, intelligent decision maker, and hybrid data P/O computer 17. P/O comparator, intelligent decision maker, and hybrid data P/O computer 17 performs recalibration of the gyroscopic sensor data using tilt sensor data, and performs all advanced multi-input P/O computations. It then sends this estimate to the ultrasound imaging system as P/O data out 33. It also generates gyroscopic drift estimates between calibrations and applies these estimates as drift data 65 to the drift indicator 66, permitting the sonographer to view and if necessary react to the drift error of the gyroscopic sensors as will be described hereinafter.

Figure 5A:
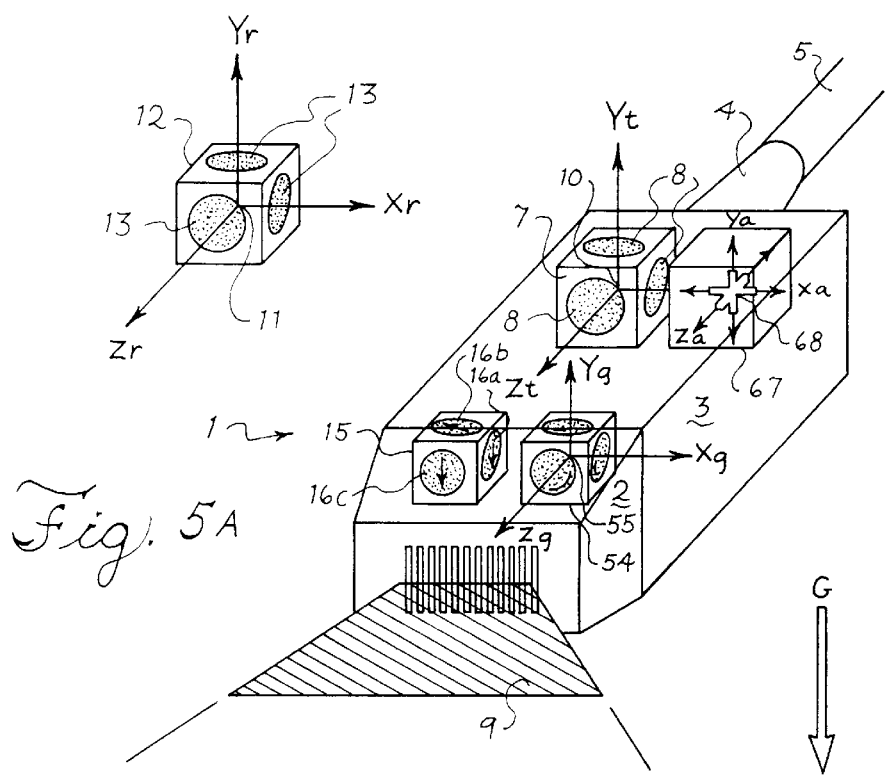
FIG. 5A illustrates a medical ultrasound system containing a hybrid positioning system which utilizes magnetic, tilt, gyroscopic, and accelerometer position and orientation subsystems according to a fourth preferred embodiment of the present invention.

FIG. 5A shows a transducer probe similar to that shown in FIG. 4A except for the incorporation of an additional accelerometer position sensing subsystem depicted by sensor array 67. Accelerometer array 67 is schematically indicated as having three orthogonally oriented accelerometers capable of reporting relative position movements of transducer probe 1. While the parallel alignment of each of the three orthogonally oriented accelerometers of accelerometer array 67 with one of the three orthogonally oriented fluxgates 8 of magnetic sensor array 7 is shown, it should be clear to anyone skilled in the art that parallel alignment of the sensors is not required in order to relate 3 axis translations of one sensor array to the other. It should be equally obvious that the sensors within each array do not necessarily need to be orthogonal to each other. In a preferred embodiment accelerometers of the type AMD-CK/0A2, available from Access Sensors SA, and described further in U.S. Pat. No. 5,353,354 are appropriate for this application.

A hybrid system containing both a magnetic subsystem and an accelerometer subsystem, and a system to intelligently and dynamically re-calibrate the accelerometer subsystem detected positions using magnetic subsystem detected position data, is capable of yielding highly accurate relative position estimates that can be recalibrated to less accurate but absolute positional estimates using position data from the magnetic subsystem. Recalibrations would be performed at appropriate times, such as during a non-imaging interval between the acquisition of 2 independent 3D data sets, so as not to introduce a position recalibration artifact in the middle of a data set.

Figure 5B:
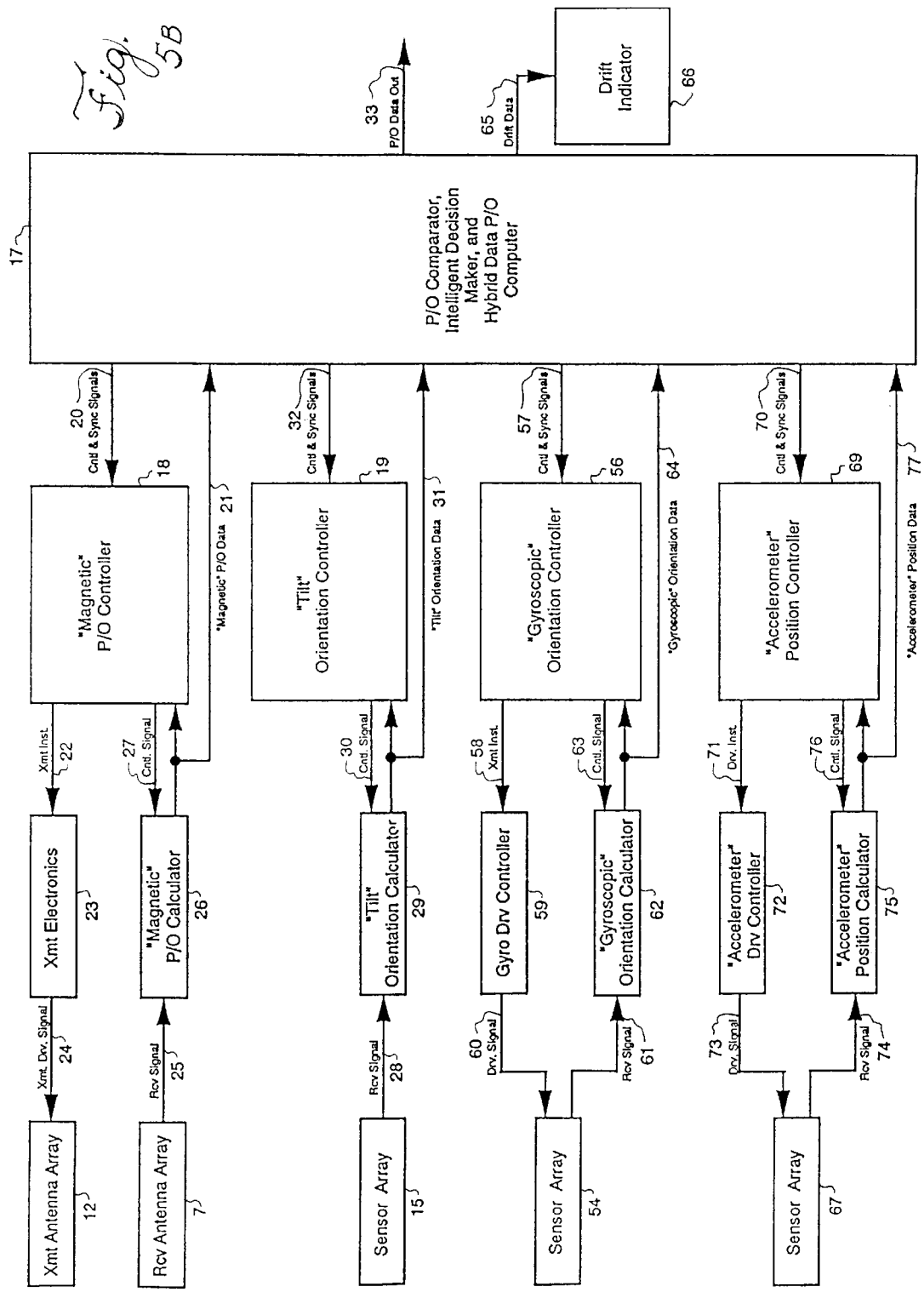
FIG. 5B illustrates a block diagram of a hybrid positioning system for the ultrasound system shown in FIG. 5A.

FIG. 5B illustrates a block diagram of a hybrid P/O system for the ultrasound system shown in FIG. 5A. The presentation of the magnetic, tilt, and gyroscopic subsystems, and the drift indicator, have not changed from their presentation in FIG. 4B. Added, is the control system for the accelerometer subsystem. The P/O comparator, intelligent decision maker, and hybrid data P/O computer 17 controls the acceleration position controller 69 by means of control, data, and synchronization signals 70. The accelerometer position controller 69 generates and sends drive instructions 71 to the accelerometer drive controller 72 and control signal 76 to accelerometer position calculator 75. Accelerometer drive controller 72 applies a drive signal 73 to the gyroscopic sensor array 67. Positional translations are sensed by the array and converted to receive signal 74 and sent to the accelerometer position calculator 75 that performs the integration process necessary to convert signal 74 into relative position estimates. The computed accelerometer position data 77 is applied to the accelerometer position controller 69, where it is used in the feedback control of the subsystem, and to P/O comparator, intelligent decision maker, and hybrid data P/O computer 17. P/O comparator, intelligent decision maker, and hybrid data P/O computer 17 performs recalibration of the accelerometer data using magnetic sensor data, and performs all advanced multi-input P/O computations. It then sends this estimate to the ultrasound imaging system as P/O data out 33. It also generates accelerometer drift estimates between calibrations and applies these estimates as drift data 65 to the drift indicator 66, permitting the sonographer to view and if necessary react to the drift error of the accelerometers.

Figure 6A:
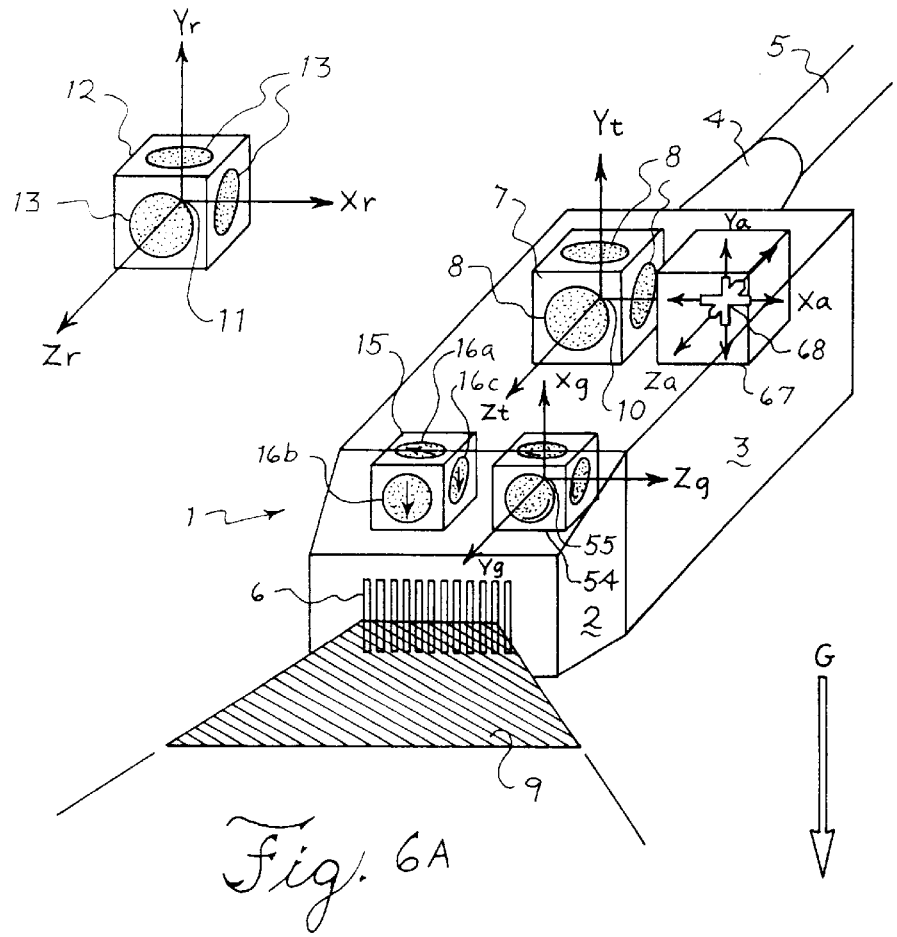
FIG. 6A illustrates a medical ultrasound transducer probe containing a hybrid positioning system which utilizes magnetic, tilt, gyroscopic, and accelerometer position and orientation subsystems according to a fifth preferred embodiment of the present invention.

FIG. 6A illustrates a transducer probe similar to that shown in FIG. 5A except for the incorporation of an actuator to automatically re-orient tilt sensor array 15 and gyroscopic array 54 depicted in FIG. 6A by rotating the sensors about two axes, i.e., change of coordinate axes of sensor arrays 15 and 54. While the parallel alignment of the paired sensors of sensor arrays 15 and 54, and coupled two axis rotations of the two sensor arrays has been shown, it should be clear to anyone of ordinary skill in the art that parallel alignment of the sensors is not required in order to relate 1, 2, or 3 axis rotations of one sensor array to the other, that the sensors within each array do not necessarily need to be orthogonal to each other, and that it is not necessary to rotate the tilt sensor in order to re-calibrate the gyroscopic sensor.

A hybrid system containing both tilt and gyroscopic orientation subsystems, and a system to re-orient the gyroscopic sensor array 54, or more preferably, 2 axis re-orientation of both the gyroscopic 54 and tilt 15 sensor arrays, relative to the transducer probe case 3, is capable of automatically performing the re-orientations of sensor 54 required to re-calibrate each gyroscopic sensor with accurate tilt sensor data. The size of currently available gyroscopic sensors makes it difficult to pack the gyroscopic sensors into a reasonably sized transducer probe case. Adding two axis rotation requirements to the design would make the task of ergonomic probe design difficult. Research is already underway to reduce the size of gyroscopic sensor arrays however, and in the future, it is expected that two axis actuator rotations of gyroscopes will be possible within appropriately sized ergonomic transducer probe cases. Polytec PI, Inc. of Costa Mesa, Calif. manufactures a PM-SG line of piezoelectric motors. These motors incorporate an annular design piezoelectric ceramic stator, the inner surface of which is held in high fiction contact with the outer surface of the rotor placed inside the annular stator. Modifications to this design, for example, could lead to an attractive two axis actuator capable of satisfying the requirements of the present invention. The two axis actuator of this example might consist of two concentric yet orthogonal annular piezoelectric motors having different annular radii, the smaller motor being contained within the inner annulus of the larger motor with the plane of its annulus oriented orthogonal to the plane of the larger motor's annulus. It is clear that any actuator means to accomplish single or multiple axis rotations will satisfy the requirements of the present invention.

As previously discussed with reference to FIG. 4A, tilt sensors cannot detect rotations about the earth's gravitational field vector G, and it is periodically necessary to re-orient gyroscopic sensor 54, both gyroscopic array 54 and tilt sensor array 15, or transducer probe 1 containing gyroscopic sensor array 54 and tilt sensor array 15, to alter the alignment of the gyroscopic sensor array with the earth's gravitational field vector G. Re-alignment of the gyroscopic sensors with G permits each gyroscopic sensor in the array to become sufficiently misaligned with G that it can be recalibrated using tilt sensor data. All decisions and control of the actuators and recalibration process is preferably the responsibility of the P/O comparator, intelligent decision maker, and hybrid data P/O computer 17 shown in FIG. 6B.

FIG. 6B illustrates a block diagram of a hybrid P/O system containing the magnetic, tilt, gyroscopic, accelerometer subsystems, and actuators of FIG. 6A. The presentation of the magnetic, tilt, gyroscopic, and accelerometer subsystems, and the drift indicator have not changed from their presentation in FIG. 5B. Added, are actuators 79 and 81 for re-orientation of the tilt and gyroscopic sensor arrays.

In the system shown in FIG. 6B, data is available from four subsystems in the form of signals 21, 31, 64, and 77. It is the responsibility of P/O comparator, intelligent decision maker, and hybrid data P/O computer 17 to decide when recalibrations are necessary, to perform re-orientations of the tilt and gyroscopic sensor arrays, and perform all computations necessary to conduct the recalibration, ending with an update of the calibration parameters for each gyroscopic sensor. The tilt sensor is re-oriented by means of the tilt 2 axis actuator control and actuators 79 following instructions provided by tilt 2 axis orientation control signal 78. The gyroscopic sensor is re-oriented by means of the gyroscopic 2 axis actuator control and actuators 81 following instructions provided by gyroscopic 2 axis orientation control signal 80.

Figure 7:
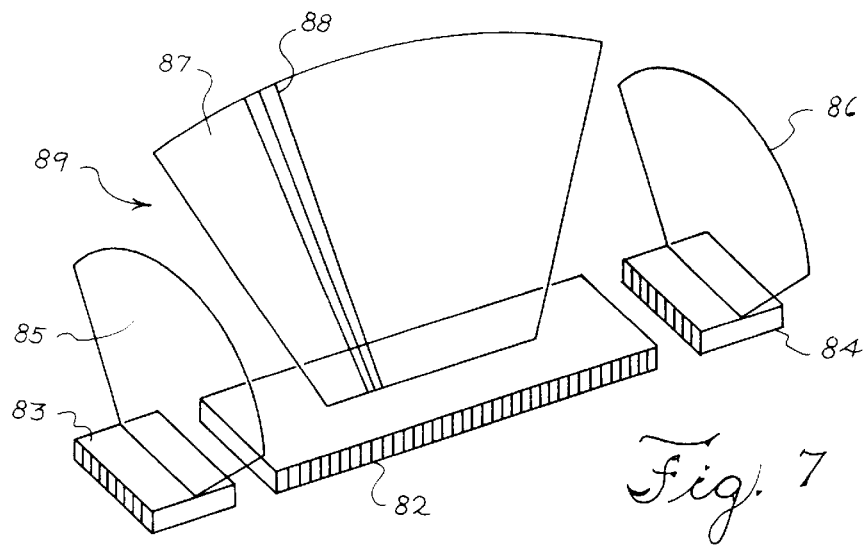
FIG. 7 illustrates an image tracking position and orientation subsystem that derives position and orientation information from images scanned by the position and orientation sensed device.

FIG. 7 illustrates an image tracking P/O subsystem 89 that derives P/O information from images scanned by the P/O sensed device. In the preferred embodiment shown in FIG. 7, the transducer includes three transducer arrays, 82, 83 and 84. The array 82 generates image data while arrays 82, 83 and 84 generate position and orientation data. The imagery P/O subsystem 89 is capable of calculating P/O estimates based on images 87, 85, and 86, created from scanline data, example scanline 88 acquired using ultrasound transducer arrays 82, 83, and 84. The imagery subsystem is taught in U.S. Ser. No. 08/621,561 entitled "Multiple Image Registration System, Method and Transducer," filed Mar. 25, 1996.

Imagery subsystems like the one shown in FIG. 7 are capable of sensing 6 degrees of freedom (DOF). They can be quite accurate when image frames are taken frequently enough, compared to the translation or rotation of the transducer probe containing arrays 82, 83, and 84, that the translations or rotations do not move image planes 85, 86, and 87 by a significant portion of the correlation length of speckle pattern in the images of image planes 85, 86, and 87. When motions are too great, the imagery system can no longer unambiguously track the speckle pattern and P/O sensing accuracy begins to fail abruptly. Use of other sensing subsystems, for example, a magnetic P/O subsystem, in combination with the imagery subsystem, in a hybrid P/O sensing system, can greatly extend the useful translation and rotation ranges detectable by the imagery subsystem. In a preferred embodiment utilizing a magnetic subsystem, the magnetic subsystem would supply all coarse P/O estimates. The images in image planes 85, 86, and 87 are then shifted, in plane, by amounts prescribed by comparison of the current coarse magnetic P/O estimate with the previous coarse magnetic P/O estimate. The imagery subsystem then takes over again correlating the current images with the shifted versions of the previous images to generate fine resolution P/O estimates. U.S. Pat. No. 5,538,004 to Bamber describes a method by which a P/O sensing device is used to detect the motion of a transducer probe between successive image plane acquisitions permitting the images to be shifted by the amount determined by the P/O system before being summed with previous images. This technique is aimed at stabilizing images, not at improving the P/O estimate, and is therefore not a description of a hybrid P/O system.

A preferred embodiment of the present invention provides for a system to correct for electromagnetic or magnetic interference and their influence on magnetic spatial positioners by using additional magnetic receiver sensor arrays fixed spatially relative to the magnetic P/O subsystem's transmit array. These additional receiver arrays are used to measure perturbations to the transmitter's field pattern and report these perturbations to a correction computer responsible for compensating for the perturbations. Interferences may be passive or active and commonly arise from metallic or magnetic objects brought into close proximity to the P/O device's magnetic receiver array, or worse yet, placed between the transmit array and the receiver array.

Additional receive arrays placed about the examination room and fixed spatially relative to the known and typically fixed position of the transmit array can be used to sense and measure perturbations to the transmit array's field pattern that result from motions of magnetic or metallic materials within the field or from any undesired electromagnetic signals generated within the field by active devices. It is always best to place the additional arrays close to the transmit array and the receive array located in the P/O sensed device, beyond that, placement depends primarily on the type of perturbations anticipated for a given application as will the algorithms to detect the perturbations and compensate for them.

As a simple example of this preferred embodiment, since electromagnetic P/O systems routinely measure and compensate for the static field present before the transmit array begins its transmit sequence, the static field could be measured by an additional array through the 3D acquisition process to ensure that the additional array measures no change in field pattern during the quiescent portion of the transmit sequence. If no changes are measured, the 3D data set from the acquisition session can be accepted (at least with regards to the accuracy of the P/O data), and if a change is detected, the data from the session could be discarded and subsequently re-acquired.

Figure 8:
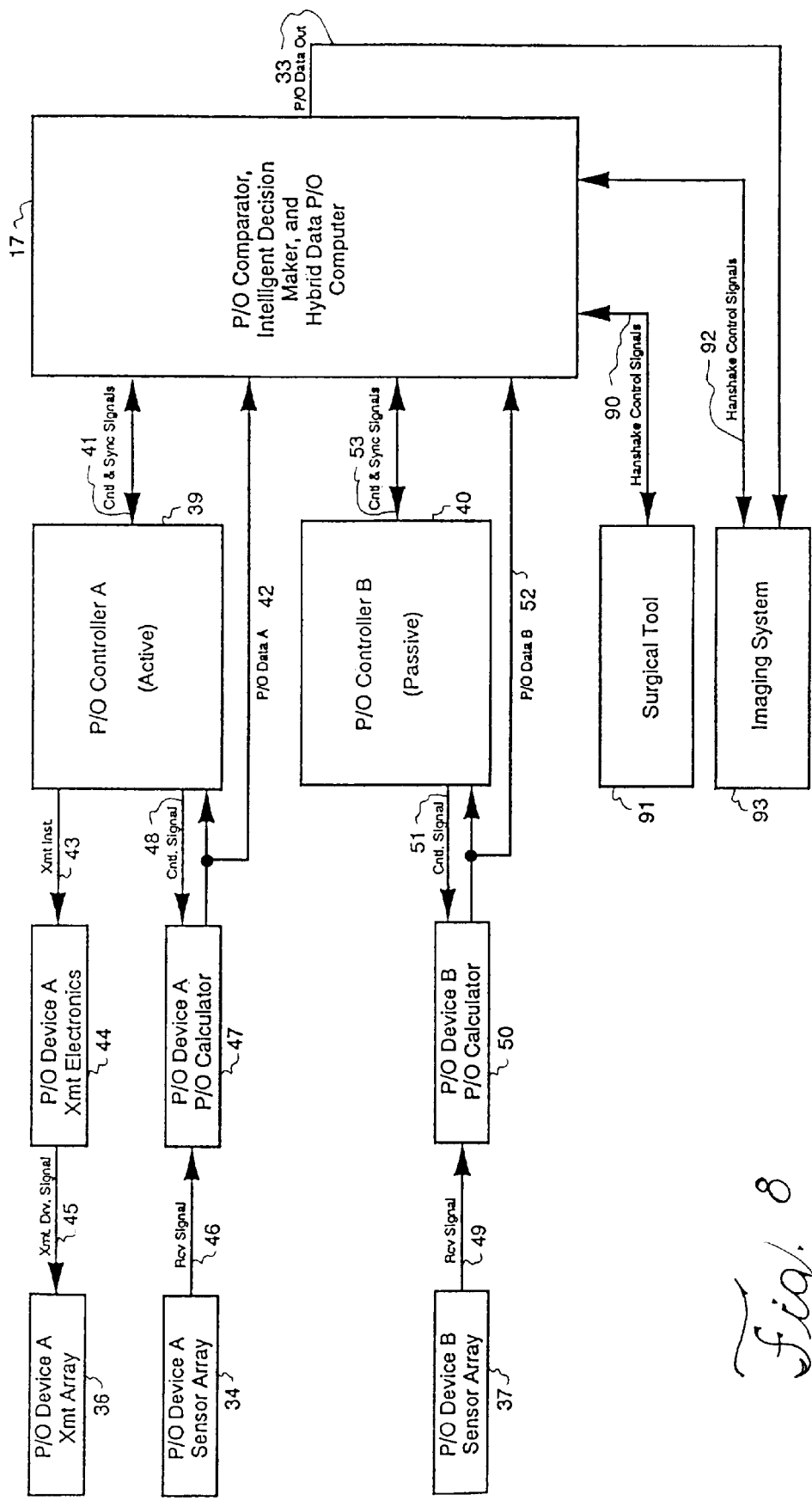
FIG. 8 illustrates a block diagram depicting synchronization of the hybrid position and orientation-system with other devices, and the imaging system.

FIG. 8 illustrates a block diagram depicting synchronization of the hybrid P/O system with other devices and the imaging system. In a preferred embodiment of the present invention the active electromagnetic interference created by competing devices is corrected by synchronizing all competing devices imaging system, the P/O system, and the surgical systems. FIG. 8 is unchanged from FIG. 3B except for the additions of handshake control signals 90 and 92, surgical tool 91, and imaging system 93. It is understood that the scope of the present invention is not limited to the particular synchronization shown in FIG. 8. Synchronization control of any two or more systems may be required and is covered by the present invention.

Synchronization of all systems used during an ultrasound exam and associated medical procedures may be required to keep interferences from one system from corrupting the operation of another system. For example, it may be necessary to stop imaging with an ultrasound transducer probe while conducting P/O system measurements to prevent interference from the ultrasound system from corrupting the P/O measurements. It may similarly be necessary to stop use of a surgical instrument, such as an electrocautery knife. It will be the responsibility of the P/O comparator, intelligent decision maker, and hybrid data P/O computer 17 to make all synchronization decisions and to generate, send, receive, and interpret all handshake signals 41, 53, 90, and 92 with the controlled systems 39, 40, 91, and 93.

Figure 9A:
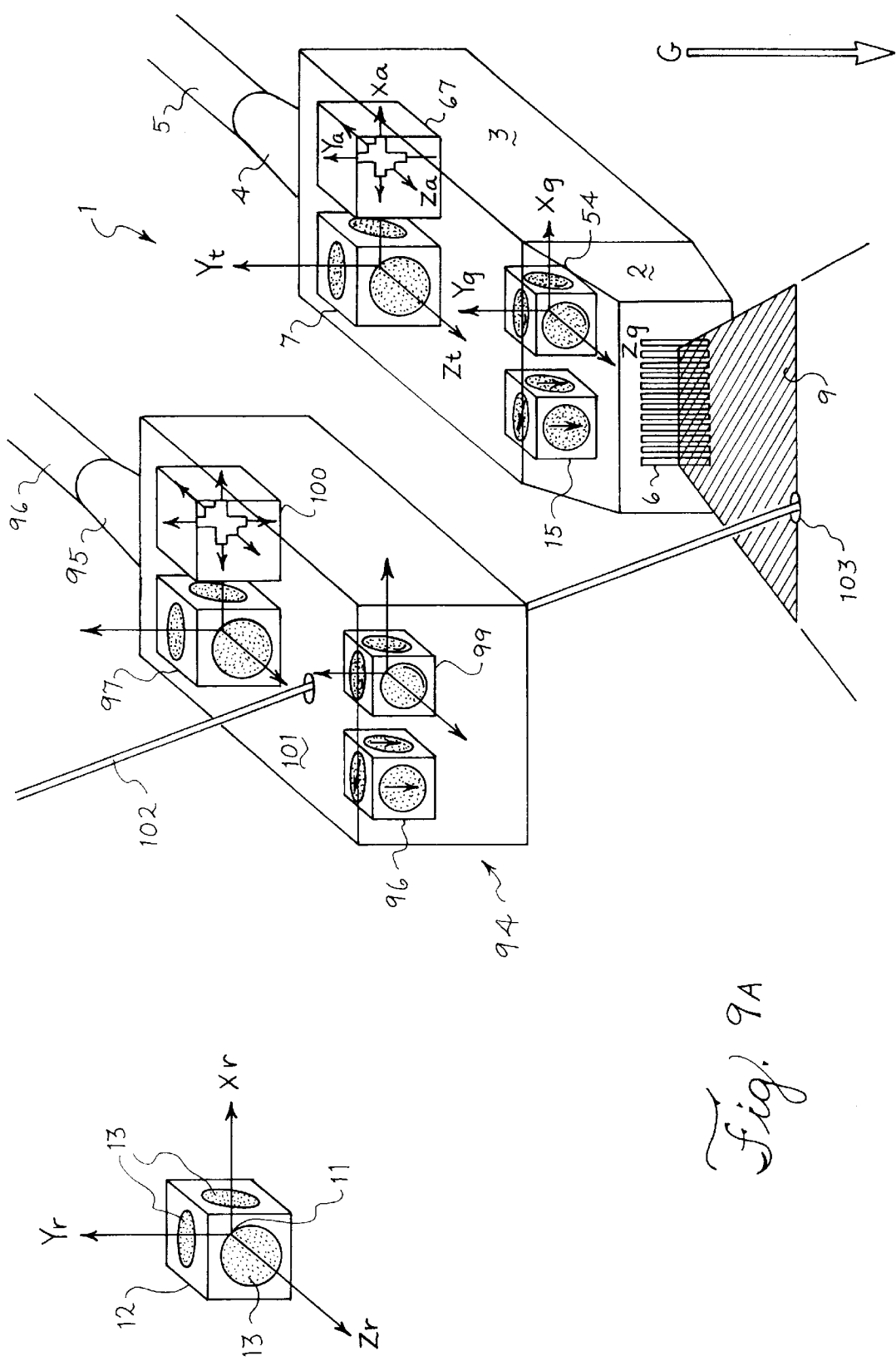
FIG. 9A illustrates a sixth preferred embodiment of the present invention by showing simultaneous use of a position and orientation sensed transducer probe with a position and orientation sensed surgical instrument for the purpose of determining the relative position and orientation of the transducer probe to the surgical instrument.

FIG. 9A illustrates a sixth preferred embodiment of the present invention by showing simultaneous use of a P/O sensed transducer probe 1 with a P/O sensed surgical instrument 94 for the purpose of determining the relative P/O of transducer probe 1 to surgical instrument 94. This preferred embodiment of the present invention allows for the determination of the relative P/O of two or more P/O sensed devices. In the example shown, the P/O configuration shown in FIG. 5A which includes magnetic arrays 7 & 97, tilt arrays 15 & 98, gyroscopic arrays 54 & 99, and accelerometer array 67 & 100 P/O subsystems is used in both the transducer probe 1 and the surgical instrument 94. The relative P/O of any two or more P/O sensed instruments can be determined and the P/O systems used do not all need to have similar designs and subsystems, and that any of the subsystems may be constructed using a non-hybrid (single subsystem) design, or may be a hybrid system constructed using any two or more P/O subsystems.

In this preferred embodiment a surgical needle guide 94 is used with transducer probe 1. In particular, the patient may be undergoing a tissue biopsy. Transducer probe 1 is used to scan the patient producing image 9 in which can be seen the tissue the physician desires to biopsy by withdrawing a small piece of the tissue with needle 102. During the biopsy procedure, it is important for the physician to know where the tip 103 of needle 102 is at all times relative to the tissue of the patient's body. This can be accomplished by providing a way to report to the physician the position of the needle tip relative to image 9. The physician can then dynamically reposition the transducer probe 1, and thus image 9, needle 102 and thus needle tip 103, relative to the patient to continually visualize needle tip 103 in image 9 while the needle is inserted through intervening tissues into the tissue to be biopsied. The task of determining the relative position of image 9 with respect to needle tip 103 can be accomplished using P/O sensed transducer probe 1, P/O sensed needle guide 94, and rigid needle 102. Also included are needle guide case 101, strain relief 95, and cable 96.

FIG. 9B illustrates a block diagram of the system shown in of FIG. 9A. The heart of this system is a relative P/O computer 110 placed between the P/O comparator, intelligent decision maker, and hybrid data P/O computers, 17 and 106, and the imaging system 93. At the request of imaging system 93, via system control signal 129, the relative P/O computer requests, via control, data, and synchronization signal 133, and receives imaging transducer probe P/O data 33 from the imaging transducer P/O comparator, intelligent decision maker, and hybrid data P/O computer 17. It also requests, via control, data and synchronization signal 134, and receives surgical device P/O data 109 from the surgical device P/O comparator, intelligent decision maker, and hybrid data P/O computer 106. It then performs relative position calculations based on these values and the known and rigid geometries of transducer probe 1 and surgical device 94. It then reports the computed relative P/O data 111 to imaging system 93 where it can be reported to the user, typically by, but not limited to, placing a mark on image 9. The P/O control, data, and synchronization signals for all P/O subsystems used in the imaging system have been lumped into imaging transducer probe P/O control, data, and synchronization signals 104, and similarly into the surgical device P/O control, data, and synchronization signals 107 for the surgical device. The P/O data from all subsystems is lumped into imaging transducer probe P/O data 105 for the imaging system and into surgical device P/O data 108 for the surgical device.

Figure 10:
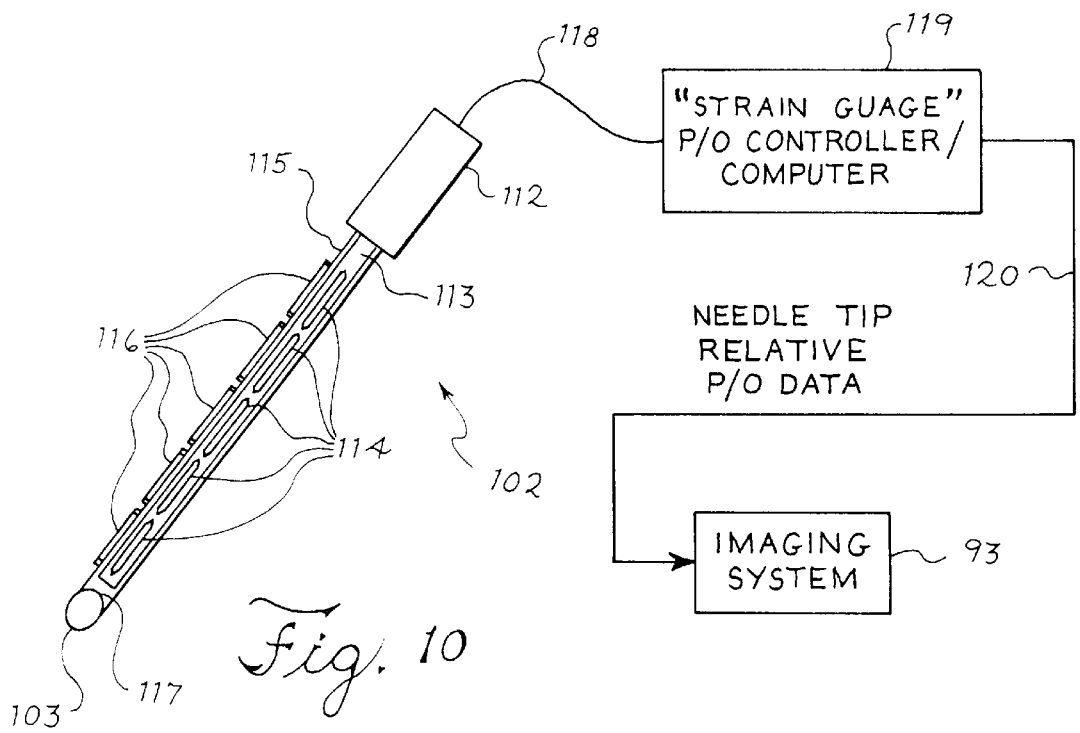
FIG. 10 illustrates a seventh preferred embodiment of the present invention of a non-rigid needle employing a strain gauge to determine the flexing of the needle such that the position of the needle tip relative to the needle handle and thus relative to the examination room or position and orientation sensed imaging transducer probe is determined.

Because real world needles are not rigid, if the system described for FIGS. 9A and B is to work, there must be a way to determine the relative P/O between the needle tip 103 and the needle handle 112. FIG. 10 illustrates a seventh preferred embodiment of the present invention by showing a non-rigid needle employing a strain gauge to determine the flexing of the needle such that the position of needle tip 103 can be determined relative to needle handle 112 and thus relative to the examination room or P/O sensed imaging transducer probe. It will be needle handle 112 that mates with a registration device (not shown) in needle guide handle 101 of FIG. 9A. In a preferred embodiment the use of strain gauge arrays 114 and 116 connected electrically to needle handle 112, and then to cable 118, by cables 113 and 115 allows for the determination of relative position between needle tip 103 and needle handle 112. Strain gauge arrays 114 and 116 are placed on orthogonal sides, or sufficiently orthogonal sides to permit measurement of all deflections of needle shaft 117 and have sufficiently fine segmentation to accurately detect all anticipated deflections of any segment of needle shaft 117 regardless of the shape of the deflection, single arc deflection, multiple arc deflections, multiple direction deflections, multiple axis deflections, or otherwise. Model SG-2/350-LY47K strain gauges available from Amega Engineering, Inc. located at One Omega Drive, Box 4047, Stanford, Conn. 06907 may be used.

Needle 102 is connected to strain gauge P/O controller/computer 119 by cable 118. Strain gauge P/O controller/computer 119 receives all data from the strain gauges and computes the P/O of needle tip 103 relative to needle handle 112 and reports this relative P/O data to the imaging system in the form of needle tip relative P/O data 120 when it is requested to do so by the imaging system via system control signal 130.

FIG. 11 illustrates an eighth preferred embodiment of the present invention by introducing use of tilt sensors for orientation sensing in an ultrasound transducer probe. In a preferred embodiment an endorectal application is illustrated to demonstrate this novel use of tilt sensors. Some applications, like the endorectal transducer probe example shown, do not require knowledge of position translations or three axes of orientation data. For these applications, one or two axes of orientation data is acceptable, and a tilt orientation system is the right choice. We have shown use of a 3 tilt sensor array 15 using tilt sensors 16a,b,c, capable of detecting orientations of any axis of the transducer probe that is held reasonably orthogonal to the earth's gravitational field vector G.

As a clinical example, an endorectal ultrasound transducer probe 1 shown in FIG. 11 for imaging the prostate gland is inserted into the rectum and rotated back and forth to sweep out a three dimensional image volume. This calls for a very sensitive rotation, requiring sensitive angular detection, and tilt sensor 15 serves this need perfectly. The sonographer might hold the long axis of the transducer probe reasonably level (orthogonal to G) and fan image 9 over the tissue being studied in a 3D exam by rotating the transducer probe about its long axis. Tilt sensor 16a would provide the desired orientation information for the rotation, and the output from all tilt sensors could be examined to ensure that the sonographer did not unintentionally rotate the transducer probe about its other axes while conducting the scan.

It will be recognized that for a transducer probe such as the endorectal transducer probe wherein only rotational motion is utilized one may do the entire tracking job with one or more tilt sensors 16 but in a more general application for a transducer probe, 1, translational motions are undergone which even 3 axis tilt sensor 15 is incapable of monitoring. Thus, our hybrid system shown in FIG. 2A is optimally suited for this general application.

Figure 12A:
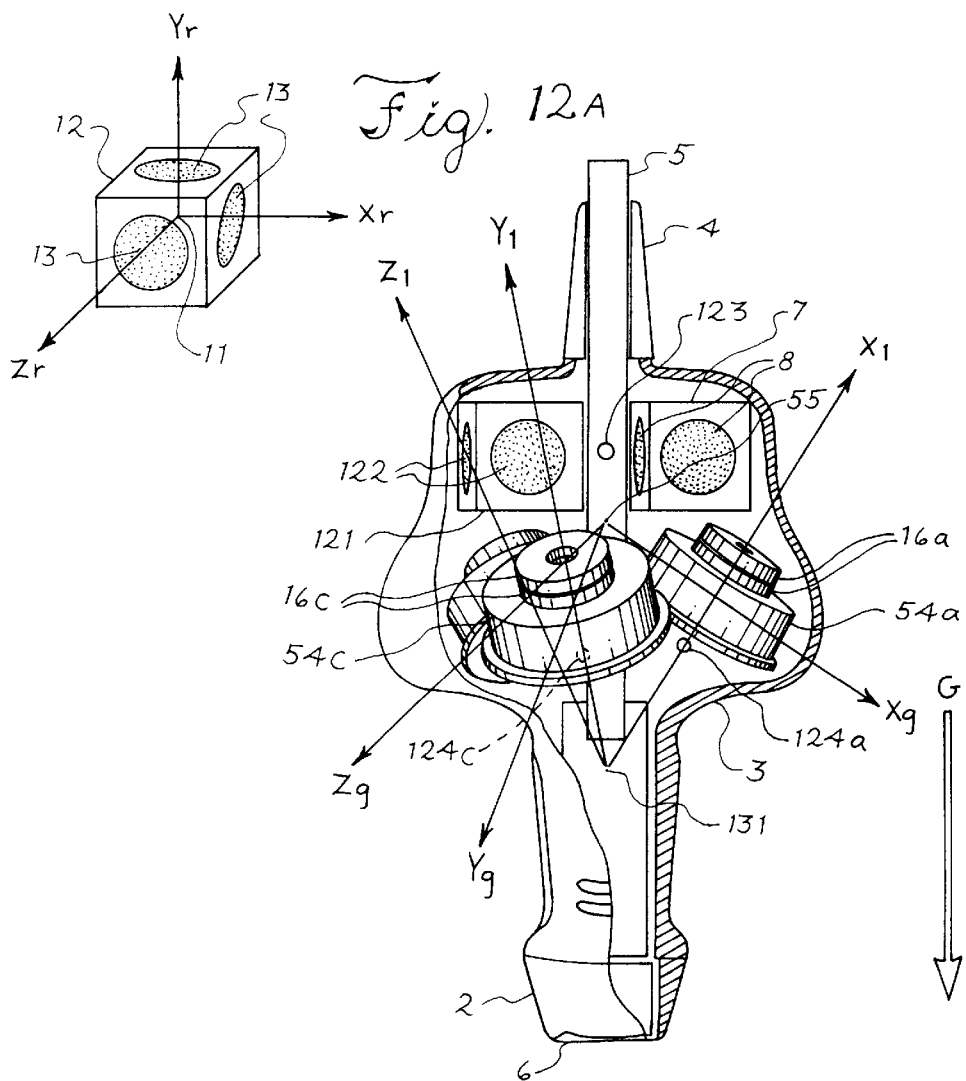
FIG. 12A illustrates a ninth preferred embodiment of the present invention for cardiology transducer applications.

FIG. 12A illustrates a ninth preferred embodiment of the present invention for cardiac applications. It shows a transducer probe similar to that shown in FIG. 4A. The transducer probe illustrated in FIG. 12A has been designed with devices currently available. To create room for these devices, many compromises were required, including a near tripling of the transducer case volume and a realignment of the coordinate systems for the tilt and gyroscopic sensors. Research has already produced smaller sensor arrays and is continuing to shrink the size of these sensor arrays. Thus it is reasonable to expect in the future that, the transducer case swelling will be subtle and parallel alignment of all coordinate systems should be possible (but of course not necessary). Also included in this design are thermistors 123, 124a, 124b (not shown), and 124c. These thermistors permit thermal monitoring of the sensor arrays.

Gyroscopic sensor array 54 is schematically indicated as having three orthogonal gyroscopes capable of reporting relative angular movements of transducer probe 1. Due to packaging constraints, the reference coordinate system for gyroscopic sensor array 54 has been moved to center 55 with axes $X_g$, $Y_g$, and $Z_g$ aligned as shown. In a preferred embodiment the gyroscopes used in this design are model QRS11-00100-101 available from Systron Donner Inertial Division.

Tilt sensor array 16 has been given its own unique reference coordinate system 131 as well, again due to packing constraints. It is preferable, but not required, to maintain right hand coordinate systems. Maintenance of right hand coordinate systems requires, for example that tilt sensor $Z_t$ be placed on top of gyroscopic sensor $Y_g$ once we have arbitrarily decided to match tilt sensor $X_t$ with gyroscopic sensor $X_g$. In a preferred embodiment each tilt sensor 16a, 16b (not shown), and 16c, is composed of two Series 0728 Micro-Arc Proportional Linear Sensors available from The Fredericks Company. Each of the two Micro-Arc Proportional Linear Sensors, used to construct each tilt sensor, are rotated 90° from each other, about their sensing axis, to ensure high sensitivity 360° angular detection.

Two magnetic sensor arrays, 7 and 121, have been used in this design. Use of two sensor arrays guarantees that at least one of the sensor arrays will have line of sight access to transmitter array 12 without risk of shielding from transducer cable 5. Proper placement of transmitter array 12 in the room, having given consideration to the predominant orientation that transducer 1 will have during the exam, will ensure that electromagnetic sensor arrays 7 and 121 are not shielded from electromagnetic transmitter array 12 by any other components of transducer 1. In a preferred embodiment the electromagnetic arrays used in this design are available from Ascension Technology Corporation, P.O. Box 527, Burlington, Vt. 05402. The transmitter array is model 600205. The receiver arrays are model 600001-B. This system provides 0.5 degree RMS angular accuracy, 0.1 degree RMS angular resolution (at 12"), 0.1" RMS translational accuracy, and 0.03" translational resolution, over a 6" translational range, 360 degrees of azimuth and roll, and 180 degrees of elevation. In a preferred embodiment, thermistors 123, and 124a,b,c are model #45004 thermistors from Yellow Springs Instruments Inc., Yellow Springs, Ohio 45387.

Figure 12B:
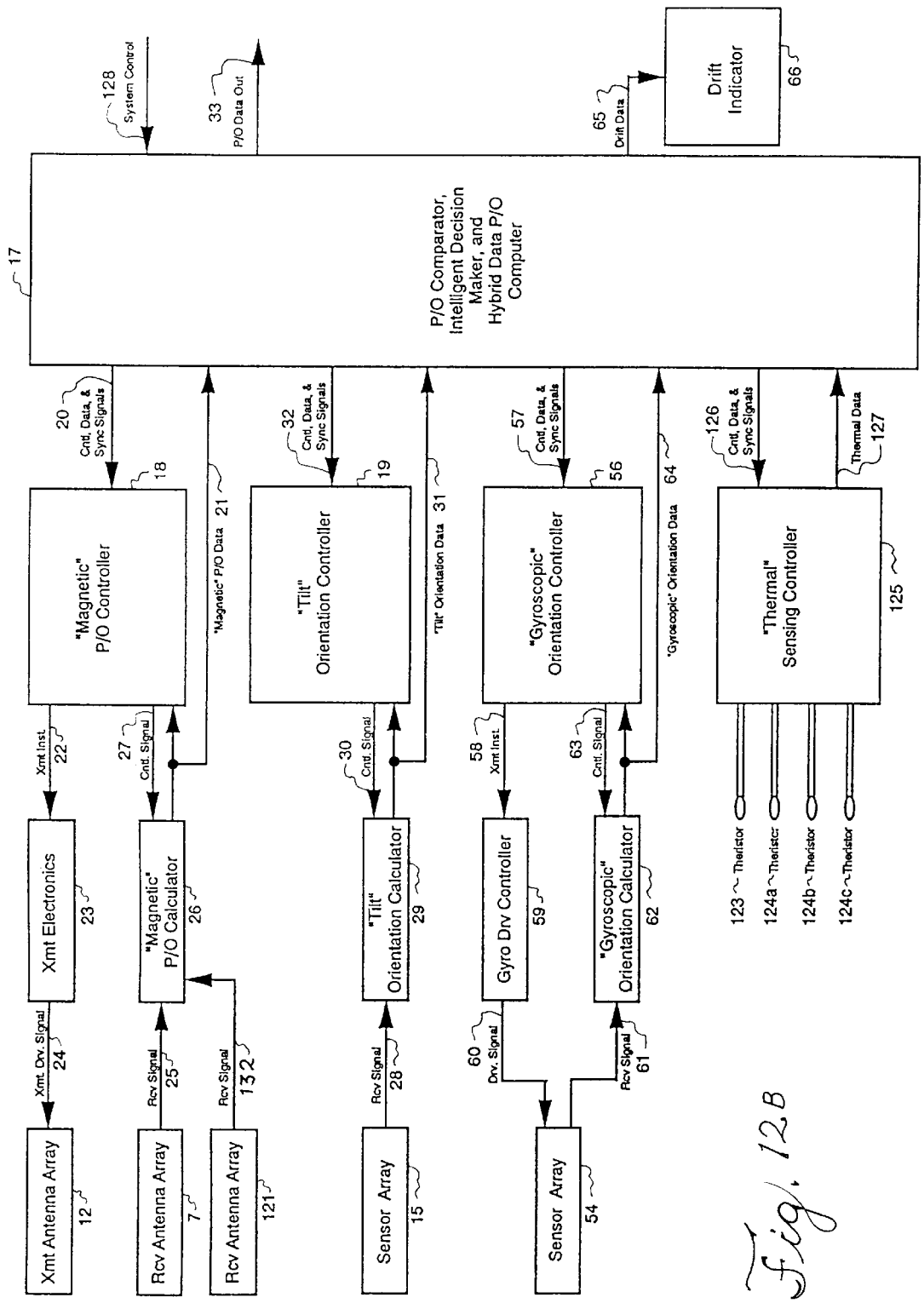
FIG. 12B illustrates a block diagram of the system shown in FIG. 12A.

FIG. 12B illustrates a block diagram of the system shown in FIG. 12A. The presentation of the tilt and gyroscopic subsystems has not changed from their presentation in FIG. 4B. Added are a second magnetic receiver array 121 to the magnetic subsystem, and the thermal sensing subsystem composed of thermal sensing controller 125 and thermistors 123, and 124a,b,c. Additional receiver array 121 in the magnetic subsystem is identical to receiver array 7 except for its position in transducer case 3. Magnetic P/O calculator 26 receives input from both sensor arrays, calculates 6 DOF P/O data from each sensor, and then reports the data to magnetic P/O controller 18 and P/O comparator, intelligent decision maker, and hybrid data P/O computer 17.

The P/O comparator, intelligent decision maker, and hybrid data P/O computer 17 receives thermal data 127 from thermal sensing controller 125 whenever requested via control, data, and synchronization signals 126. P/O comparator, intelligent decision maker, and hybrid data P/O computer 17 delivers the thermal data to controllers 18, 19, and 56 via control, data, and synchronization signals 20, 32, and 57 respectively, permitting each controller to use the thermal data to compensate the output of each sensor by applying thermal correction data obtained, for example, from a look up table stored in each controller. Thermistors 123, and 124a,b,c, are passive devices that continually deliver thermal sensing information to thermal sensing controller 125.

A detailed description of the operation of the preferred embodiment shown in FIGS. 12A and 12B now follows. At power up of the ultrasound imaging system (not shown), of which the hybrid positioning system of this invention is a component, P/O comparator, intelligent decision maker, and hybrid data P/O computer 17 receives a self test initiate command from the ultrasound imaging system and initiates a self test of itself and all of its subsystems. Self test of arrays 12, 7, 121, 15, and 54, and thermistors 123, and 124a,b,c will also be conducted if hybrid P/O sensing transducer probe 1 is connected to the system at power up.

P/O comparator, intelligent decision maker, and hybrid data P/O computer 17 receives an initiate measurements command via system control and synchronization signal 128 shortly after hybrid P/O sensing transducer probe 1 is connected to the ultrasound imaging system (not shown). After receiving the initiate measurements command, P/O comparator, intelligent decision maker, and hybrid data P/O computer 17, instructs controllers 18, 19, 56, and 125 to test arrays 12, 7, 121, 15, and 54, and thermistors 123, and 124,a,b,c; initializes all of its registers, commands controllers 18, 19, 56, and 125 to do the same, and the entire hybrid P/O system begins measuring and tracking the P/O of transducer probe 1.

Data is continuously available from tilt orientation controller 19, gyroscopic orientation controller 56, and thermal sensing controller 125, but is available only after completion of each magnetic subsystem measurement cycle from magnetic P/O controller 18. It is therefore the measurement cycle time of the magnetic subsystem that sets the pace of the hybrid P/O system.

P/O comparator, intelligent decision maker, and hybrid data P/O computer 17 initiates a measurement cycle by transmitting a measurement value request to all controllers via control, data, and synchronization signal paths 20, 32, 57, and 126. It then waits for new data and data valid signals from each controller which will be received via data lines 21, 31, 64, and 127.

After receipt of each measurement data update from the controllers, P/O comparator, intelligent decision maker, and hybrid data P/O computer 17, compares all P/O estimates, computes its best estimate of hybrid P/O, and updates the next available set of registers it uses to store hybrid P/O data. The best estimate for the time at which the data used to estimate the hybrid P/O data was measured is also stored with the hybrid P/O data. There are two or more sets of registers used to store hybrid P/O estimate data sets, making the most recent estimate and the previous estimate available to P/O comparator, intelligent decision maker, and hybrid data P/O computer 17 at all times. P/O comparator, intelligent decision maker, and hybrid data P/O computer 17 uses all available hybrid P/O estimates, and the transmit time for the transmit pulse on each pulse echo data sequence (scanbeam), to estimate the P/O of probe 3 at the time of transmit. The request for probe P/O data, along with a scanbeam transmit time stamp, is received via system control path 128 shortly after transmit of the beam. P/O comparator, intelligent decision maker, and hybrid data P/O computer 17 calculates the P/O of the probe 3 at transmit and returns the data to the ultrasound imaging system via P/O data out 33 before the next beam is fired. The ultrasound imaging system combines the P/O estimate and transmit time with known scan geometry parameters to calculate and store the scanbeam origin position, scanbeam orientation, and transmit time, for every scanbeam used by the ultrasound imaging system while, for example, scanning image planes like plane 9 shown in FIG. 1A. Some applications may require access to P/O and time stamp estimates for subscanbeam components, such as, for example, the data received on a single transducer element, or subgroup of transducer elements, during acquisition of the scanbeam. When required by the application, the ultrasound imaging system will calculate and store unique P/O and time stamp estimates for each of the required sub-scanbeam components. Other applications may require less P/O data and may not require P/O data to be stored for each scanbeam. For these applications, P/O data for groupings of scanbeams only may be stored. For example: the P/O and time stamp data for each Doppler scanline, which is calculated using the data from more than one scanbeam may be stored. In other words, the sub-scanframe component types for which the P/O and time stamp data will be calculated and stored, will be selected to be appropriate for each application. Also the data in each of these data sets may be compensated, using the P/O and time stamp data from the current and previous data sets, before storing the data set. For example, the detected Doppler velocity for a scanline may be compensated based on the known velocity and/or acceleration of the transducer probe during acquisition of the scanline as determined from the P/O and time stamps for each of the scanbeams used to calculate the Doppler velocity for the scanline. These compensations may also be performed later in the process. Also estimates for other parameters calculated from the available P/O estimates for each sub-frame component, such as velocity or acceleration estimates may be stored. In the configurations using an accelerometer, acceleration can be measured directly and velocity can be calculated by integrating the acceleration.

P/O comparator, intelligent decision maker, and hybrid data P/O computer 17 may also report its most recent hybrid P/O estimate and/or individual estimates of position and/or orientation received from one subsystem controller to any other subsystem controller. Access to the additional P/O estimates permits each controller to better determine when the data it receives from its sensors is valid or invalid, and permits it to better optimize its own P/O estimates or to re-calibrate itself with the aid of the additional P/O data received from the other controllers. The details of the optimization and recalibration process are complex and involved. They also depend on the relative placement of the sensors in the hybrid P/O transducer probe case 3.

The magnetic P/O subsystem can always provide a coarse absolute (relative to the fixed transmitter array 12) 6 DOF P/O estimate regardless of its P/O as long as one of its sensors 7 or 121 has an unobstructed electromagnetic view of transmitter array 12. As discussed earlier, careful placement of transmitter array 12 in the room guarantees the required unobstructed view. The tilt orientation subsystem provides fine absolute orientation estimates for all orientations except for rotations about the earth's gravitation field vector G. The gyroscopic orientation subsystem provides fine relative orientation estimates regardless of its orientation.

Each gyroscopic sensor in array 54 provides a voltage that is proportional to its angular velocity to gyroscopic orientation calculator 62. Gyroscopic orientation calculator 62 continually integrates this voltage to determine the orientation of each sensor relative to the orientation it had and the time of its last calibration. Unfortunately, this process is not without error, causing the calibration of the gyroscopic sensors to drift over time. The gyroscopic sensors must be periodically recalibrated.

If a 3D data acquisition session is not in progress on the ultrasound imaging system, and P/O comparator, intelligent decision maker, and hybrid data P/O computer 17, after examining the P/O data from the magnetic P/O subsystem, decides that the measurement axis of a gyroscopic sensor, 54a,b, or c, is sufficiently misaligned with the earth's gravitational field vector G that valid tilt sensor data will be available for this orientation, it can initiate recalibration of the gyroscopic sensor using the absolute orientation data received from tilt orientation calculator 29. The timing diagram for this process is presented in FIG. 13.

Figure 13:
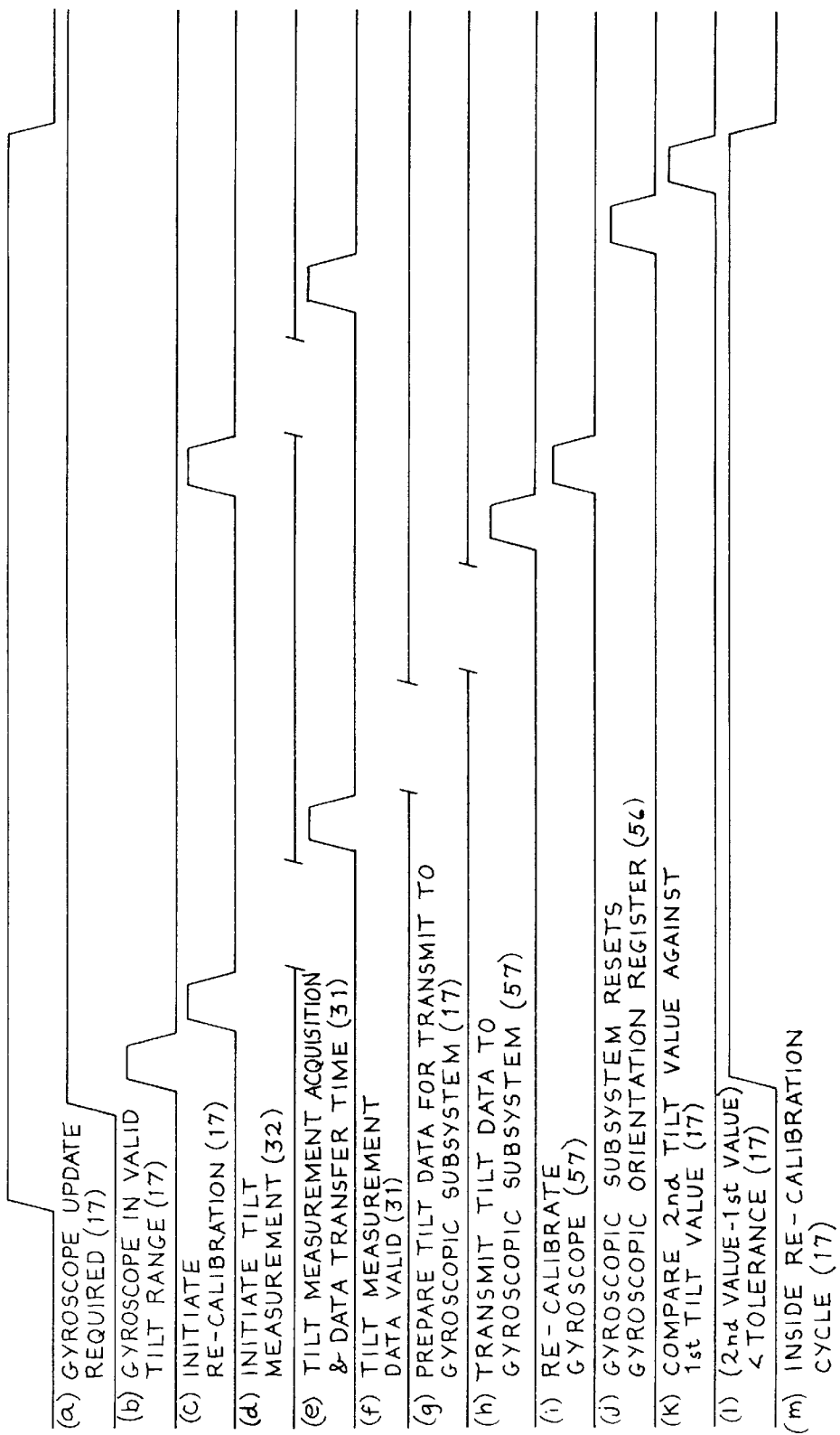
FIG. 13 illustrates a timing diagram for the recalibration of gyroscopic sensors using tilt sensor data.

As seen in FIG. 13, following a predetermined drift time-out period subsequent to the last recalibration of a particular gyroscope, P/O comparator, intelligent decision maker, and hybrid data P/O computer 17 generates an internal gyroscope update required signal (a) for that particular gyroscope. The other two gyroscopes operate in parallel to what is being described here. In the example shown in FIG. 13, at the time signal (a) changes from low (logic state 0) to high (logic state 1), signal (b), gyroscope in valid tilt range, is still low. Some time later, the sonographer randomly rotates transducer probe 1 into a valid tilt range for this gyroscope and signal (b) transitions to high. Signal (c) then changes to high initiating recalibration. An initiate tilt measurement signal is sent out over control, data, and synchronization signal path 32, signal (d), and time is allowed for tilt orientation controller 19 to request, receive, process, and transmit new tilt data. The new data is returned along tilt orientation data signal path 31 to P/O comparator, intelligent decision maker, and hybrid data P/O computer 17. When a data valid signal is received over this same data path, signal (f), P/O comparator, intelligent decision maker, and hybrid data P/O computer 17 prepares the data and transmits it to gyroscopic orientation controller 56 over control, data, and synchronization signal path 57. When data transfer is complete, a re-calibrate gyroscope signal, (i) is sent over this same signal path. This causes gyroscopic orientation controller 56 to request and confirm recalibration of the orientation register for the gyroscope, signal (j). Signal (d) transitions once again when signal (j) transitions, initiating a second tilt measurement to be acquired. When the new tilt data is valid, signal (f) transitions again, while signal (m), inside calibration cycle, is high indicating that a recalibration cycle is still in progress, and causing signal (k) to transition. The transition of signal k causes P/O comparator, intelligent decision maker, and hybrid data P/O computer 17 to compare the new tilt value with the previous tilt value. If the difference of these two values is less than a predetermined tolerance value, signal (l) transitions, resetting signals (a) and (m) and concluding the recalibration cycle.

Since the tilt sensors can never measure orientations about the earth's gravitational field vector G, any gyroscopic sensor sufficiently aligned with G to be in an invalid tilt sensor range cannot be recalibrated using tilt sensor data. The gyroscopic sensors selected for use in this design let them maintain <0.2 degrees of drift over a 100 second interval. Given the low drift rate of these gyroscopes, it is likely that the sonographer will rotate transducer probe 1 sufficiently during the normal process of conducting an ultrasound exam to permit all three gyroscopic sensors to be updated at sufficiently frequent intervals to limit their drift errors to acceptable levels. As soon as the sonographer randomly rotates each gyroscopic sensor into the range of valid tilt sensor orientations, P/O comparator, intelligent decision maker, and hybrid data P/O computer 17 will initiate the gyroscopes recalibration.

Gyroscopic sensor drift for each gyroscopic sensor 54a, b,c is continually calculated by gyroscopic orientation controller 56 and reported to P/O comparator, intelligent decision maker, and hybrid data P/O computer 17 which in turn, reports the drift data 65 to drift indicator 66 for display to the sonographer.

If P/O comparator, intelligent decision maker, and hybrid data P/O computer 17 ever determines that the drift error of a particular gyroscopic sensor is too great and that the gyroscopic sensor is still not within a valid tilt sensor range, it can send a warning signal to drift indicator 66 via drift data path 65 causing display of a warning message to the sonographer prompting the sonographer to take actions to permit recalibration of the offending gyroscopic array. The action required by the sonographer will be to rotate the transducer, in any direction away from G to permit recalibration of the offending gyroscopic sensor. Recalibration procedures are accomplished outside the normal hybrid P/O measurement cycle and therefore can run at a rate limited only by the measurement and data transfer rates of the tilt and gyroscopic subsystems with P/O comparator, intelligent decision maker, and hybrid data P/O computer 17. Calibration time will be sufficiently rapid to let us safely assume that transducer probe 1 does not move between the time the tilt data is recorded and the time the gyroscope is recalibrated. As a precaution however, the tilt orientation is remeasured following recalibration of the gyroscope to ensure that transducer probe 1 has moved by no more that a predetermined tolerance level during the recalibration process.

In summary, multiple preferred embodiments of the present invention have been disclosed. In a preferred embodiment, a tilt sensor array is combined with magnetic sensor array. The sensors are complimentary in that they utilize different physical principles and/or different algorithms to track different motion parameters. Because of this the tilt, or orientation, aspects of the spatial addresses are improved beyond that which a pure magnetic system is capable of delivering, particularly when metal or electromagnetic interferences are present.

Other preferred embodiments do not limit the hybrid positioning system of the present invention to the combination of tilt sensors and magnetic sensors. All combinations of sensors wherein two or more sensor types each measures its own motion parameter using its own measuring principle thus providing a superior overall spatial address not obtainable from the single sensor type. Further beneficial combinations include, for example, inertial sensors such as accelerometers and gyroscopes combined with magnetic sensors and tilt sensors. An important distinguishing point of the present invention is that different spatial parameters are monitored by different sensors and that some information available from an inferior sensor may be ignored in favor of superior information from an independent sensor utilizing entirely different sensing principles for example in the tilt/magnetic example wherein the magnetically reported angular information may be ignored. This is a multisensor solution wherein algorithms are available to accept and digest the inputs from the multiple sensors and provide superior spatial addresses based on the best strengths of each sensor.

In addition one may dynamically or selectively reconfigure which sensor is used under which conditions, or one may utilize all available data from all of the sensors used in a device, all the time.

In a preferred embodiment inertial sensors which include various gyroscopes and accelerometers are combined with magnetic sensors. As a specific sub-example gyros are frequently utilized as extremely sensitive angular motion (rotation or tilting) detectors and could be used for orientation in combination with the magnetic sensor which would detect translational motions. Specifically, gyroscopes could detect angles and a magnetic positioner could detect translation positions. When further used in combination with tilt sensors and accelerometers, tilt sensors can be used to re-calibrate the absolute orientation for gyroscopic sensors and magnetic sensors can be used to re-calibrate the absolute position of accelerometers.

One may deduce something about the motion of the transducer probe by monitoring the changes to the imagery appearing on the monitor. Various image correlation techniques may be used to compare image frames and deduce the motion of the transducer probe between such frames. One advantage of image-based techniques is that they account for any undesirable patient motion. See U.S. Ser. No. 08/621,561 referred to above. This application describes a variety of such image-based techniques. A hybrid system may be constructed according to the present invention using the combination of tilt sensors and image-based sensing. Translations could be monitored via imagery and tilts by the tilt meters for example. Some advantages of such a system would be (a) for pure tilting motions no image-based computational power is required, (b) for combined motions only translations need be computed from imagery and the imaging array(s) and image-based motion algorithms may be optimized for translation only.

In another embodiment, optical trackers involve optically tracking the motion(s) of the transducer probe. One way is to image the transducer probe itself (or some distinguishing marks on it) using one or more camera means and have software compute the motions based on the apparent changes to the transducer probe image. Other less sophisticated optical means involve optically tracking the motion of specific transducer probe points such as optical reflectors or light emitting diodes. Such optical means could be used in combination with inertial means, the inertial means also offering redundancy when the optical means lightpath is broken.

Thus, the sensors used in the various preferred embodiments measure P/O parameters. A P/O parameter is defined as either position data, orientation data or both.

It is to be understood that the forms of the invention described herewith are to be taken as preferred examples and that various changes in the shape, size and arrangement of parts may be resorted to, without departing from the spirit of the invention or scope of the claims.

What is claimed is:

1. A movable medical imaging device having sensors for measuring the position and orientation of the movable device, the device comprising:
    a first sensor disposed on the movable device for measuring a first position and orientation (P/O) parameter; and
    a second sensor of a different type than said first sensor, the second sensor disposed on the movable device wherein the second sensor measures a second P/O parameter that is different from the first P/O parameter.

2. The device according to claim 1 wherein the first sensor is a tilt sensor that measures an angular orientation of the device relative to gravity and the second sensor is a magnetic sensor that measures at least one angular orientation and a translational position of the device relative to a reference point.

3. The device according to claim 2 wherein the tilt sensor measures the angular orientation about two axes and the magnetic sensor measures the angular orientation about one axis and the translational position along three axes.

4. The device according to claim 2 wherein the tilt sensor measures the angular orientation of the device about two axes and the magnetic sensor measures the angular orientation about two axes and the translational position of the device along three axes.

5. The device according to claim 2 further comprising a gyroscopic sensor disposed on the movable device for measuring the rotation of the device.

6. The device according to claim 5 further comprising an accelerometer sensor disposed on the movable device for measuring the acceleration of the device.

7. The device according to claim 1 wherein the first sensor is a tilt sensor that measures an angular orientation of the device relative to gravity and the second sensor is a magnetic sensor that measures a translational position of the device relative to a reference point.

8. The device according to claim 1 wherein the first sensor is an active device and the second sensor is a passive device.

9. The device according to claim 8 wherein the first sensor receives transmitted signals from a transmitter remotely located from the device.

10. The device according to claim 1 wherein the first and second sensors are active devices.

11. The device according to claim 1 wherein the first and second sensors are passive devices.

12. The device according to claim 1 wherein the second sensor measures the same first P/O parameter as the first sensor.

13. The device according to claim 12 further comprising means for determining which of the measurements from the first sensor or the second sensor will be used in calculating position or orientation of the device.

14. A system for tracking the position and orientation a movable medical imaging device, the system comprising:
    a first sensor disposed on the movable device wherein the first sensor measures a first position and orientation (P/O) parameter;
    a second sensor of a different type than said first sensor, the second sensor disposed on the movable device wherein the second sensor measures a second P/O parameter;
    a transmit array located remotely from the movable device; and
    a computer coupled to the transmit array, the first sensor and the second sensor wherein the computer instructs the transmit array to transmit signals that are received by the first sensor and the computer receives signals from the first sensor indicative of the first P/O parameter and from the second sensor indicative of the second P/O parameter.

15. The system according to claim 14 wherein the first P/O parameter is a position parameter of the movable device and the second P/O parameter is an orientation parameter of the movable device.

16. The system according to claim 14 wherein the first P/O parameter is a first position parameter and the second P/O parameter is a second position parameter different from the first position parameter.

17. The system according to claim 14 wherein the first P/O parameter is a first orientation parameter and the second P/O parameter is a second orientation parameter different from the first orientation parameter.

18. The system according to claim 14 wherein the second sensor also measures the first P/O parameter.

19. The system according to claim 18 wherein the computer also receives signals from the second sensor indicative of the first P/O parameter and determines which of the signals it receives from the first and second sensor will be used for the first P/O parameter.

20. The system according to claim 18 wherein the first P/O parameter measured by the second sensor is used to improve the measurement of the first P/O parameter measured by the first sensor.

21. The system according to claim 14 further comprising means to compute an improved first P/O parameter based upon the second P/O parameter.

22. A system according to claim 14 further comprising a display coupled to the computer for displaying the position and orientation of the movable device.

23. A system according to claim 14 further comprising:
an orientation controller coupled to the computer wherein the orientation controller receives control, data, and synchronization signals from the computer;
an orientation calculator coupled between the orientation controller and the first sensor wherein the orientation calculator receives control signals from the orientation controller and receives orientation signals from the first sensor and outputs orientation data to the computer;
a position and orientation controller coupled to the controller wherein the position and orientation controller receives control, data, and synchronization signals from the computer; and
a position and orientation calculator coupled between the position and orientation controller and the second sensor wherein the position and orientation calculator receives control signals from the position and orientation controller and receives position and orientation signals from the second sensor and outputs position and orientation data to the computer.

24. The system according to claim 14 wherein the first sensor is a magnetic sensor and the second sensor is a tilt sensor.

25. The system according to claim 24 further comprising a gyroscopic sensor disposed on the movable device.

26. The system according to claim 25 further comprising a drift indicator coupled to the gyroscopic sensor to indicate drift in the gyroscope sensor.

27. The system according to claim 25 further comprising an accelerometer disposed on the device.

28. The system according to claim 27 further comprising means for recalibrating the accelerometer with signals received from the magnetic sensor.

29. The system according to claim 25 further comprising means for recalibrating the gyroscopic sensor with signals received from the tilt sensor.

30. The system according to claim 29 further comprising a display for indicating that the gyroscopic sensor needs recalibration.

31. The system according to claim 29 wherein said means for recalibration include actuators for rotating the gyroscopic sensor relative to the movable device.

32. The system according to claim 25 further comprising means for recalibrating the gyroscopic sensor with signals received from the magnetic sensor.

33. The system according to claim 14 further comprising a gyroscopic sensor and an accelerometer both disposed on the movable device.

34. The system according to claim 14 wherein the first sensor is a magnetic sensor and the second sensor is an accelerometer.

35. A position and orientation system for tracking spatial parameters of a medical implement, the system comprising:
a first subsystem disposed on the medical implement having a sensor of a first type for measuring at least one degree of freedom of the medical implement; and
a second subsystem disposed on the medical implement having a sensor of a second type that is different from the sensor of the first type for measuring at least one degree of freedom of the medical implement.

36. The system according to claim 35 wherein the sensor of the first type is a magnetic sensor and the sensor of the second type is a tilt sensor.

37. The system according to claim 35 wherein the sensor of the first type is a magnetic sensor and the sensor of the second type is a gyroscopic sensor.

38. The system according to claim 35 wherein the sensor of the first type is a magnetic sensor and the sensor of the second type is an accelerometer.

39. The system according to claim 38 wherein measurements from the magnetic sensor are used to recalibrate the accelerometer.

40. The system according to claim 35 further comprising:
a third subsystem disposed on the medical implement having a sensor of a third type that is different from the sensors of the first and second type for measuring at least one degree of freedom of the medical implement.

41. The system according to claim 40 wherein the sensor of the third type is a gyroscope.

42. The system according to claim 40 wherein the sensor of the third type is an accelerometer.

43. The orientation system according to claim 40 further comprising:
a fourth subsystem disposed on the medical implement having a sensor of a fourth type that is different from the sensors of the first, second and third type for measuring at least one degree of freedom of the medical implement.

44. The system according to claim 43 wherein the sensor of the first type is a magnetic sensor, the sensor of the second type is a tilt sensor, the sensor of the third type is a gyroscopic sensor and the sensor of the fourth type is an accelerometer.

45. The system according to claim 44 wherein measurements from the tilt sensor are used to recalibrate the gyroscopic sensor.

46. The system according to claim 44 wherein measurements from the magnetic sensor are used to recalibrate the accelerometer.

47. The system according to claim 35 further comprising a computer coupled to the medical implement wherein said first and second subsystems transmit their measured signals to the computer which computes the position and orientation of the medical implement.

48. The system according to claim 47 wherein the sensor of the first type measures six degrees of freedom of the medical implement, however, the computer never uses more than five of the six degrees of freedom measured in its computations.

49. The system according to claim 48 wherein at least one of the degrees of freedom measured by the first type of sensor and the second type of sensor are redundant and the computer determines which will be used in the computation of position and orientation of the medical implement.

50. A position and orientation system for tracking the relative positions of a medical implement with respect to a medical imaging device, the system comprising:

a first subsystem disposed on the medical implement for measuring at least one degree of freedom of the medical implement and a second subsystem different from the first subsystem disposed on the medical implement for measuring at least one degree of freedom of the medical implement;

a third subsystem disposed on the medical imaging device for measuring at least one degree of freedom of the medical imaging device and a fourth subsystem different from the third subsystem disposed on the medical imaging device for measuring at least one degree of freedom of the medical imaging device; and a computer coupled to the first, second, third and fourth subsystem which receives measured signals from the first, second, third and fourth subsystems and computes the relative position of the medical implement with respect to the medical imaging device.

51. The system according to claim 50 wherein the medical imaging device is an ultrasound transducer and the medical implement is a surgical tool.

52. The system according to claim 51 wherein the surgical tool is a biopsy needle.

53. The system according to claim 51 wherein the medical implement is a deformable device.

54. A method of tracking the position and orientation of a movable medical imaging device, the method comprising the steps of:

providing a first sensor disposed on the movable medical imaging device;

providing a second sensor of a different type than the first sensor, the second sensor disposed on the movable device;

measuring a first Position and Orientation (P/O) parameter with the first sensor; and measuring a second P/O parameter with the second sensor.

55. The method according to claim 54 wherein said second P/O parameter is different from said first P/O parameter of motion.

56. The method according to claim 54 further comprising the steps of:

measuring six P/O parameters with the first sensor; and computing position and orientation data using no more than five P/O parameters measured by the first sensor.

57. A method of tracking the position and orientation of a movable medical imaging device, the method comprising the steps of:

measuring the position and orientation of the medical imaging device;

transmitting the position and orientation measurements to an imaging system;

measuring subframe data;

transmitting subframe data to the imaging system;

tagging the transmitted subframe data with a time stamp;

transmitting the time stamped transmitted subframe data;

storing the subframe data, time stamp and position and orientation measurements;

calculating the origin position of the subframe data, the orientation of the subframe data and transmit time for the subframe data.

58. A method according to claim 57 wherein the step of measuring subframe data consists of a single scanline.

59. A method according to claim 57 wherein the step of measuring subframe data includes interpolating color Doppler scanlines.

60. A method according to claim 57 wherein the step of measuring subframe data includes interpolating between subframe data of any type.

61. A method according to claim 57 wherein the step of measuring subframe data includes measuring data received on a single transducer element.

62. A method according to claim 57 wherein the step of measuring subframe data includes data from a group of transducer elements.

63. A method according to claim 57 wherein the step of measuring subframe data includes measuring a plurality of scanbeams.

64. A method according to claim 57 wherein the step of calculating involves using the scan geometry parameters for the scanbeams generated.

65. A method of tracking the position and orientation of a movable medical imaging device, the method comprising any sequence of the steps of:

providing a first sensor disposed on the movable medical imaging device;

providing a second sensor of a different type than the first sensor, the second sensor disposed on the movable medical imaging device;

measuring the position and orientation of the medical imaging device using said first and second sensors;

measuring subframe data; and associating the measured position and orientation with the subframe data.

66. The method according to claim 65 further comprising the steps of:

tagging the transmitted subframe data with a time stamp;

storing the subframe data, time stamp and position and orientation measurements; and calculating the origin position of the subframe data, the orientation of the subframe data and transmit time for the subframe data.

* * * * *

UNITED STATES PATENT AND TRADEMARK OFFICE
CERTIFICATE OF CORRECTION

PATENT NO. : 6,122,538
DATED : September 19, 2000
INVENTOR(S) : J. W. Sliwa, Jr. et al.

It is certified that error appears in the above-identified patent and that said Letters Patent is hereby corrected as shown below:

On the Title Page

Page 2, column 2, line 16, delete "Hensen" and substitute --Hansen-- in its place.

In column 13, line 1, delete "945118" and substitute --94518-- in its place.

In column 18, line 30, delete "in of FIG. 9A" and substitute -- in FIG. 9A-- in its place.

In column 22, line 14, delete "subscanbeam" and substitute -- sub-scanbeam-- in its place.

In column 22, line 64, delete "gravitation" and substitute --gravitational-- in its place.

UNITED STATES PATENT AND TRADEMARK OFFICE
CERTIFICATE OF CORRECTION

PATENT NO. : 6,122,538
DATED : September 19, 2000
INVENTOR(S) : J. W. Sliwa, Jr. et al.

It is certified that error appears in the above-identified patent and that said Letters Patent is hereby corrected as shown below:

In column 23, line 29, delete "1) ," and substitute --1),-- in its place.

In column 23, line 54, delete "signal k causes" and substitute --signal (k) causes-- in its place.

Signed and Sealed this

Eighth Day of May, 2001

Attest:

NICHOLAS P. GODICI

Attesting Officer   Acting Director of the United States Patent and Trademark Office